United States Patent [19]
Caldwell

[11] Patent Number: 5,698,303
[45] Date of Patent: Dec. 16, 1997

[54] CONTROLLING THE POROSITY AND PERMEATION OF A WEB

[75] Inventor: James M. Caldwell, Cardiff, Calif.

[73] Assignee: Nextec Applications, Inc., Carlsbad, Calif.

[21] Appl. No.: 486,212

[22] Filed: Jun. 7, 1995

Related U.S. Application Data

[63] Continuation-in-part of Ser. No. 472,568, Jun. 7, 1995, which is a continuation-in-part of Ser. No. 442,983, May 17, 1995, which is a continuation-in-part of Ser. No. 407,191, Mar. 17, 1995, which is a continuation-in-part of Ser. No. 17,855, Feb. 16, 1993, Pat. No. 5,418,051, which is a continuation-in-part of Ser. No. 680,645, Apr. 2, 1991, Pat. No. 5,209,965, which is a continuation-in-part of Ser. No. 319,778, Mar. 10, 1989, Pat. No. 5,004,643, which is a continuation of Ser. No. 167,630, Mar. 14, 1988, abandoned, Ser. No. 167,643, Mar. 14, 1988, abandoned, Ser. No. 167,797, Mar. 14, 1988, abandoned, and Ser. No. 167,869, Mar. 14, 1988, abandoned.

[51] Int. Cl.$^6$ .................................................. B32B 7/02
[52] U.S. Cl. .............................. 428/215; 428/216; 528/15
[58] Field of Search .................................. 427/498, 501, 427/512, 513, 551, 558, 559, 595, 230, 389.9, 39, 430.1; 428/215, 216; 528/15

[56] References Cited

U.S. PATENT DOCUMENTS

| | | |
|---|---|---|
| 162,332 | 4/1875 | Allen . |
| 1,281,728 | 10/1918 | Weinheim . |
| 2,117,432 | 5/1938 | Linscott . |
| 2,575,577 | 11/1951 | Beauchamp . |
| 2,626,941 | 1/1953 | Liabeck . |
| 2,673,823 | 3/1954 | Biefeld et al. . |
| 2,759,900 | 8/1956 | Caldwell et al. . |
| 2,773,050 | 12/1956 | Caldwell et al. . |
| 2,839,479 | 7/1958 | Caldwell et al. . |
| 2,865,790 | 12/1958 | Baer . |
| 2,893,962 | 7/1959 | Bartell . |
| 2,956,884 | 10/1960 | Caldwell . |
| 2,976,182 | 3/1961 | Caldwell et al. . |
| 3,026,293 | 3/1962 | Caldwell et al. . |
| 3,165,423 | 1/1965 | Caldwell et al. . |
| 3,184,421 | 5/1965 | Caldwell et al. . |
| 3,265,529 | 8/1966 | Caldwell et al. . |
| 3,326,713 | 6/1967 | Smith . |

(List continued on next page.)

FOREIGN PATENT DOCUMENTS

| | | |
|---|---|---|
| 57-149559 | 9/1982 | Japan . |
| 422469 | 9/1974 | Russian Federation . |
| 8908553 | 9/1989 | WIPO . |
| 8908554 | 9/1989 | WIPO . |
| 8908555 | 9/1989 | WIPO . |

OTHER PUBLICATIONS

Dr. Radko Krema and Kollektiv, "Übersicht über die Einsatzgebiete von Textilverbundstoffen", *Textilverbundstoffe*, 249–252, Veb Dachbuchverlag, Leibzig, DE (1963).

Caldwell and Dannelly, "Vapor-Permeable, Water-Resistant Fabrics,"*American Dyestuff Report* No. 3, pp. 25–29 (Jan. 30, 1967).

"Silicones," *Encyclopedia of Polymer Science and Engineering*, 2nd edition, Wiley, New York v. 15, pp. 234–255 (1985–1990).

*Primary Examiner*—Michael Lusignan
*Attorney, Agent, or Firm*—Lyon & Lyon LLP

[57] ABSTRACT

Products and methods for controlling the porosity and permeation of a web are provided using a curable thixotropic shear thinnable polymer composition that preferably encapsulates a plurality of fibers of the web and/or forms an internal layer within the web. Webs suitable for several different uses are featured, for example medical garments resistant to permeation by a virus or bacteria. The effective pore size of the web is controlled by regulating various factors such as the thickness of the polymer composition encapsulating the fibers and the thickness and placement of the internal polymer layer. Other factors include the polymer density, structure, and crosslinking orientation, as well as the diffusion, permeation and sorption of the polymer.

6 Claims, 6 Drawing Sheets

U.S. PATENT DOCUMENTS

| | | |
|---|---|---|
| 3,328,661 | 6/1967 | Grebe . |
| 3,356,628 | 12/1967 | Smith . |
| 3,360,394 | 12/1967 | Griffin et al. . |
| 3,393,186 | 7/1968 | Groves et al. . |
| 3,398,182 | 8/1968 | Guenthner et al. . |
| 3,436,366 | 4/1969 | Modic . |
| 3,594,213 | 7/1971 | Rudman . |
| 3,639,155 | 2/1972 | Hartieim et al. . |
| 3,896,251 | 7/1975 | Landucci . |
| 4,032,502 | 6/1977 | Lee et al. . |
| 4,108,825 | 8/1978 | Hayes . |
| 4,110,392 | 8/1978 | Yamazaki . |
| 4,112,179 | 9/1978 | Maccalous et al. . |
| 4,162,243 | 7/1979 | Lee et al. . |
| 4,162,356 | 7/1979 | Grenoble . |
| 4,216,252 | 8/1980 | Moeller . |
| 4,216,290 | 8/1980 | De Beul et al. . |
| 4,250,075 | 2/1981 | Monroe et al. . |
| 4,287,261 | 9/1981 | West et al. . |
| 4,293,611 | 10/1981 | Martin . |
| 4,297,265 | 10/1981 | Olsen . |
| 4,311,760 | 1/1982 | Kalinowski et al. . |
| 4,329,274 | 5/1982 | Faltynek . |
| 4,369,231 | 1/1983 | West et al. . |
| 4,370,365 | 1/1983 | Takamizawa et al. . |
| 4,426,476 | 1/1984 | Chang . |
| 4,427,801 | 1/1984 | Sweet . |
| 4,442,060 | 4/1984 | Bouverot et al. . |
| 4,454,191 | 6/1984 | von Blucher et al. . |
| 4,472,470 | 9/1984 | Modic . |
| 4,478,895 | 10/1984 | Makami et al. . |
| 4,483,900 | 11/1984 | Goldfarb . |
| 4,500,584 | 2/1985 | Modic . |
| 4,500,659 | 2/1985 | Kroupa et al. . |
| 4,504,549 | 3/1985 | Pines et al. . |
| 4,539,930 | 9/1985 | Stuck et al. . |
| 4,548,859 | 10/1985 | Kline et al. . |
| 4,555,811 | 12/1985 | Shimalla . |
| 4,560,611 | 12/1985 | Naka et al. . |
| 4,562,219 | 12/1985 | Frye . |
| 4,585,830 | 4/1986 | Sweet . |
| 4,588,614 | 5/1986 | Lauchenauer . |
| 4,600,436 | 7/1986 | Traver et al. . |
| 4,619,864 | 10/1986 | Hendrix et al. . |
| 4,666,765 | 5/1987 | Caldwell et al. . |
| 4,684,570 | 8/1987 | Malaney . |
| 4,753,978 | 6/1988 | Jensen . |
| 4,758,239 | 7/1988 | Yeo et al. . |
| 4,785,047 | 11/1988 | Jensen . |
| 4,828,556 | 5/1989 | Braun et al. . |
| 4,894,105 | 1/1990 | Dyksterhouse et al. . |
| 4,919,739 | 4/1990 | Dyksterhouse et al. . |
| 5,004,643 | 4/1991 | Caldwell . |
| 5,019,062 | 5/1991 | Ryan et al. . |
| 5,102,836 | 4/1992 | Brown et al. . |
| 5,128,198 | 7/1992 | Dyksterhouse et al. . |
| 5,209,965 | 5/1993 | Caldwell . |
| 5,213,881 | 5/1993 | Timmons et al. . |
| 5,284,677 | 2/1994 | Coughlin . |
| 5,322,727 | 6/1994 | Yankus et al. . |
| 5,322,729 | 6/1994 | Heeter et al. . |
| 5,344,702 | 9/1994 | Haubs et al. . |
| 5,527,578 | 6/1996 | Mazarek et al. ............... 422/387 X |
| 5,529,822 | 6/1996 | Togeshi et al. ............... 422/387 X |

CONTROLLING THE POROSITY AND PERMEATION OF A WEB

CROSS-REFERENCE TO RELATED PATENT APPLICATIONS

This application is a continuation-in-part of U.S. patent application Ser. No. 08/472,568, filed Jun. 7, 1995, which is a continuation-in-part of U.S. patent application Ser. No. 08/442,983, filed May 17, 1995, which is a continuation-in-part application of U.S. patent application Ser. No. 08/407,191, filed on Mar. 17, 1995, which is a continuation-in-part of U.S. patent application Ser. No. 08/017,855 filed on Feb. 16, 1993, now U.S. Pat. No. 5,418,051, which is a continuation-in-part of U.S. patent application Ser. No. 07/680,645, filed Apr. 2, 1991, now U.S. Pat. No. 5,209,965, which is a continuation-in-part of U.S. patent application Ser. No. 07/319,778, filed Mar. 10, 1989, now U.S. Pat. No. 5,004,643, which is a continuation of U.S. patent application Ser. Nos. 167,630; 167,643; 167,797; and 167,869, all filed on Mar. 14, 1988 and all are now abandoned. All of the above-referenced applications are incorporated herein by reference in their entirety including any drawings.

FIELD OF THE INVENTION

The present invention relates generally to the field of webs, such as those used in garments, and more particularly to methods of treating such webs.

BACKGROUND OF THE INVENTION

None of the following is admitted to be prior art to the present invention.

Webs and fabrics, especially those used to make garments, could be vastly improved if there were a means to control the porosity or permeability of the web; although this fact has previously gone largely unrecognized. For example, a problem that has long plagued the art has been the inability to construct a rainwear garment that is waterproof, breathable and comfortable. Similarly, there is a great need for a medical gament that is breathable and comfortable but impermeable to disease causing microorganisms such as viruses and bacteria. What is needed is a single method of selectively controlling the porosity of a web that is capable of achieving any of a wide variety of desired porosities.

Articles having improved performance and functional properties are obtained at the expense of comfort and breathability. Greater comfort sacrifices maximum functionality and greater functionality sacrifices comfort. However, conventional treatments of webs with silicone resins and fluorochemicals are typically unable to solve this dilemma and fall into the general categories of (i) surface coatings; (ii) saturations or impregnations; and (iii) layers of fibers and/or polymers.

I. Coatings

Prior fluorochemical and silicone (See U.S. Pat. Nos. 3,436,366; 3,639,155; 4,472,470; 4,500,584; and 4,666,765) fabric coating treatments evidently can protect only that side of the fabric upon which they are disposed. Such treatments significantly alter the hand, or tactile feel, of the treated side. Prior silicone fabric coatings typically degrade the tactile finish, or hand, of the fabric and give the coated fabric side a rubberized finish which is not appealing for many fabric uses, particularly garments.

Other polymeric coatings have been used in prior attempts to make a garment breathable, yet waterproof. For example, U.S. Pat. No. 4,454,191 describes a waterproof and moisture-conducting fabric coated with a hydrophilic polymer. In addition, various polyorganosiloxane compositions can be used for making coatings that impart water-repellency to fabrics. For example, U.S. Pat. No. 4,370,365 describes such a product that is said to have a good "hand" and to possess waterproofness. However, it has not been shown that polyorganosiloxanes have been coated on fabrics in such a way that both high levels of resistance to water by the fibers/filaments and high levels of permeability to water vapor are achieved.

Porous webs have been further shown to be surface coated in, for example, U.S. Pat. Nos. 4,478,895; 4,112,179; 4,297,265; 2,893,962; 4,504,549; 3,360,394; 4,293,611; 4,472,470; and 4,666,765. These surface coatings impart various characteristics to the surface of a web, but remain on the surface and do not provide a film over the individual internal fibers and/or yarn bundles of the web. In addition, such coatings on the web surface tend to wash away quickly.

II. Saturation and Impregnation

Prior treatments of webs by saturation or impregnation with a polymer material, such as a silicone resin, are typically accomplished by immersion, using a low viscosity liquid silicone resin so that the low viscosity liquid can flow readily into the web, and be adsorbed or absorbed therewithin. Particularly for flexible webs, including fabric, an immersion application of a liquid or paste composition to the web is achieved, for example, by the so-called padding process wherein a fabric material is passed first through a bath and subsequently through squeeze rollers in the process sometimes called single-dip, single-nip padding. Alternatively, for example, the fabric can be passed between squeeze rollers, the bottom one of which carries the liquid or paste composition in a process sometimes called double-dip or double-nip padding.

The silicone resin treated product is typically a rubberized web, or fabric, that is very heavily impregnated with silicone. For example, U.S. Pat. No. 2,673,823 teaches impregnating a polymer into the interstices of a fabric and thus fully filling the interstices. Thus, this patent provides no control of the saturation of the fabric and instead teaches full saturation of the interstices of the fabric. Such a treated web is substantially devoid of its original tactile and visual properties, and instead has the characteristic rubbery properties of a cured silicone polymer.

Prior treatments of webs that force a composition into the spaces of the web while maintaining some breathability have relied on using low viscosity compositions or solvents to aid in the flow of the composition. U.S. Pat. No. 3,594,213 describes a process for impregnating or coating fabrics with liquified compositions to create a breathable fabric. Thus, the method of this patent imparts no energy into the composition to liquify it while forcing it into the spaces of the web, because the composition is substantially liquified before placement onto and into the web. U.S. Pat. No. 4,588,614 teaches a method for incorporating an active agent into a porous substrate. This process utilizes a solvent to aid in the incorporation of the active agent into the web. The active agent is a non-curable agent since the addition of heat aids in the reduction of viscosity.

III. Layers

Several references describe laminates or layers of fabrics and/or polymers. For example, U.S. Pat. Nos. 4,872,220; 5,024,594; 5,180,585; 5,335,372; and 5,391,423; describe articles that use layers of fabrics and/or polymers to protect against blood, microbes, and viruses from penetrating through the fabrics. Similarly, U.S. Pat. No. 4,991,232 describes a medical garment comprising a plurality of plies to prevent blood from penetrating through the garment.

IV. Additional Backround Information

One technique that does not easily fall within any of the three categories listed above (i.e., coatings, saturations, and layers) is described in Caldwell, *American Dyestuff Reporter*, 3:25–29, 1967 and U.S. Pat. No. 3,265,529, issued Aug. 9, 1966. These references describes a method for "coating" a fabric that mechanically pushes or forces a water swellable polymer below the surface of a fabric to form a discontinuous or porous layer that swells and forms a continous layer or barrier when contacted with water. It is said that an effective combination of comfort and rain protection was achieved. No indication is given that the polymer is thixotropic and it appears that the polymer does not not substantially encapsulated the structural elements of the web.

The use of polytetrafluorethylene (PTFE) has been said to produce a fabric with a large plurality of pores of about 0.2 to 0.3 microns in contrast to conventional polyurethane coatings with pore sizes in the range of 2 to 3 microns. See U.S. Pat. No. 4,483,900, issued Nov. 20, 1984.

It has been said that the addition of a peroxide can lower the viscosity of polymer used as a barrier layer in a web laminate and provide a web having pore sizes distributed predominantly in the range of 7 to 12 microns, with a lesser amount of pores from 12 to 25 microns, with virtually no pores greater than 25 microns and with a peak of pore size distribution less than 10 microns. See U.S. Pat. No. 5,213,881, issued May 25, 1993.

SUMMARY OF THE INVENTION

The present invention relates to controlling the porosity or permeation of webs by treating webs with a curable shear thinnable thixatropic polymer composition to become substantially impermeable to selected particles or molecules (while remaining permeable to other smaller particles or molecules) by controllably engineering the effective pore size of the web. For example, the effective pore size of the web can be controlled so that the web is resistant to permeation to a disease causing microorganism such as a virus or bacteria but the web is still permeable to gas molecules such as water wapor and gas molecules in the air such as oxygen.

Manipulation and alteration of the polymer composition and the web produces a web that either: (1) has some of its structural elements encapsulated by the polymer composition while at least some of the interstitial spaces of the web are open; or (2) has an internal layer extending through the web; or (3) has both encapsulated structural elements and an internal layer of polymer composition. The webs are preferably comfortable (i.e., good hand) and have improved functional properties preferably (i.e., are breathable yet water proof).

The term "encapsulated" refers to the partial or complete surrounding, encasement, or enclosing by a discrete layer, film, coating, or the like, of exposed surface portions of at least some individual fiber or lining of a cell or pore wall of a porous web. Such a layer can sometimes be contiguous or integral with other portions of the same enveloping material which becomes deposited on internal areas of a web which are adjacent to such enveloping layer, enveloped fiber, lined cell or pore wall, or the like. The thickness of the enveloping layer is generally in the range of 0.01 to 50 microns, and preferably in the range of about 0.05 to 25 microns, most preferably 0.1 to 10 microns. Measurements of the degree of envelopment, interstitial fillage, plugging, or the like in an internal coating are conveniently made by microscopy, or preferably by conventional scanning electron microscopy (SEM) techniques. Because of the nature of such measuring by SEM for purposes of the present invention, "a completely filled" interstitial space or open cell can be regarded as a "plugged" interstitial space or open cell.

The term "internal coating or internal layer" as used herein, refers to a region generally spaced from the outer surfaces of the web which is substantially continuously filled by the combination of the polymer controllably placed therein and the fibers and filaments of the web in the specified region. Such coating or layer envelopes, and/or surrounds, and/or encapsulates individual fibers, or lines cell or pore walls of the porous web or substrate, in the specified region. The internal layer is not necessarily flat but may undulate or meander through the web, occasionally even touching one or both surfaces of the web. Generally, the internal layer is exposed on both sides of a web as part of the multi complex structure of a woven and non-woven web. The thickness of the internal layer is generally in the range of 0.01 to 50 microns, and preferably in the range of about 0.05 to 25 microns, most preferably 0.1 to 10 microns.

The present invention provides methods and apparatus for controlling the effective pore size of a web as well as the articles produced by such methods and apparatus. Described in detail herein are various factors or variables that can be contolled to produce a web having the desired pore size. The term "effective pore size" refers to the overall porosity of the web and is determined by the size of the particles or molecules that can pass through the web. Thus, the measurement of the effective pore size correlates to the largest pore present in the web. The actual pore size and shape at any given point in the web will vary to some extent due to the construction of the web and the amount and type of polymer present in the web. Factors effecting the effective pore size are described herein.

In one aspect the present invention provides a method for controlling the effective pore size of a web by applying a curable thixotropic material to the web and subjecting the thixotropic material to sufficient energy to cause the thixotropic material to flow into the web and selectively position in to the web in a manner such that at least some of the interstitial spaces of the web remain open.

In another aspect, the invention provides an article comprising a web having a curable thixotropic material positioned within the web to control the effective pore size of the web.

In yet another aspect the invention provides apparatus for controlling the effective pore size of a web having a plurality of structural elements with interstitial spaces therebetween comprising: (i) a means for applying tension to the the web; (ii) a means for applying a curable shear thinnable polymer composition onto a surface of the tensioned web; (iii) means for shear thinning the polymer composition to substantially reduce its viscosity and selectively place it into the tensioned web, leaving at least some of the interstitial spaces open. Various machines and procedures can be used for performing the process of the invention. Illustrative machines and processes of use which are suitable for use in the practice of this invention, are described in U.S. application Ser. No. 08/407,191, filed Mar. 17, 1995 and hereby incorporated by reference.

I. Webs

The term "web" as used herein is intended to include fabrics and refers to a sheet-like structure (woven or non-woven) comprised of fibers or structural elements. Included with the fibers can be non-fibrous elements, such as particulate fillers, binders, dyes, sizes and the like in amounts that do not substantially affect the porosity or flexibility of the web. While preferably, at least 50 weight percent of a web treated in accordance with the present invention is fibers, more preferred webs have at least about 85 weight percent of their structure as fiber. It is presently preferred that webs be untreated with any sizing agent, coating, or the like, except as taught herein. The web may comprise a laminated film or fabric and a woven or non-woven porous substrate. The web may also be a composite film or a film laminated to a porous substrate or a double layer.

Sample webs or fabrics that are beneficially treated, fiber enveloped and internally coated in accordance with the invention include nylon, cotton, rayon and acrylic fabrics, as well as fabrics that are blends of fiber types. Sample nylon fabrics include lime ice, hot coral, raspberry pulp, and diva blue Tactel (registered trademark of ICI Americas, Inc.) fabrics available from agent Arthur Kahn, Inc. Sample cotton fabrics include Intrepid cotton cornsilk, sagebrush cotton, and light blue cotton fabrics available also from Arthur Kahn, Inc. Non-woven, monofilamentous, fabrics such as TYVEK (registered trademark of E. I. duPont de Nemours Co., Inc.) and the like are also employable. It is believed that when sufficient energy is introduced that some portion of the durable water repellent finish is removed from the pretreated web and blooms to the surface of the polymer if the polymer thin film is sufficiently thin and the viscosity and rheology is modified sufficiently during the shear thinning process step of the invention.

The fibers utilized in a porous flexible web treated by the methods and apparatus of the present invention can be of natural or synthetic origin. Mixtures of natural fibers and synthetic fibers can also be used. Examples of natural fibers include cotton, wool, silk, jute, linen, and the like. Examples of synthetic fibers include acetate, polyesters (including polyethyleneterephthalate), polyamides (including nylon), acrylics, olefins, aramids, azlons, glasses, modacrylics, novoloids, nytrils, rayons, sarans, spandex, vinal, vinyon, regenerated cellulose, cellulose acetates, and the like. Blends of natural and synthetic fibers can also be used.

The term "webs" includes flexible and non-flexible porous webs. Webs usable in the practice of this invention can be classified into two general types: (A) Fibrous webs; and (B) Substrates having open cells or pores, such as foams.

A. Fibrous Webs

A porous, flexible fibrous web is comprised of a plurality of associated or interengaged fibers or structural elements having interstices or interstitial spaces defined therebetween. Preferred fibrous webs can include woven or non-woven fabrics. Other substrates include, but are not limited to, a matrix having open cells or pores therein such as foams or synthetic leathers. A flexible porous web used as a starting material in the present invention is generally and typically, essentially planar or flat and has generally opposed, parallel facing surfaces. Such a web is a three-dimensional structure comprised of a plurality of fibers with interstices therebetween or a matrix having open cells or pores therein. The matrix can be comprised of polymeric solids including fibrous and non-fibrous elements.

B. Substrates

Three principal classes of substrates having open pores or cells may be utilized in the present invention: leathers (including natural leathers, and man-made or synthetic leathers), foamed plastic sheets (or films) having open cells, and filtration membranes.

1. Foamed Plastic Sheets

Foamed plastic sheet or film substrates are produced either by compounding a foaming agent additive with resin or by injecting air or a volatile fluid into the still liquid polymer while it is being processed into a sheet or film. A foamed substrate has an internal structure characterized by a network of gas spaces, or cells, that make such foamed substrate less dense than the solid polymer. The foamed sheets or film substrates used as starting materials in the practice of this invention are flexible, open-celled structures.

2. Leathers

Natural leathers suitable for use in this invention are typically split hides. Synthetic leathers have wide variations in composition (or structure) and properties, but they look like leather in the goods in which they are used. For purposes of technological description, synthetic leathers can be divided into two general categories: coated fabrics and poromerics.

Synthetic leathers which are poromerics are manufactured so as to resemble leather closely in breathability and moisture vapor permeability, as well as in workability, machinability, and other properties. The barrier and permeability properties normally are obtained by manufacturing a controlled microporous (open celled) structure. Synthetic leathers are coated fabrics and the coating is usually either vinyl or urethane. Vinyl coatings can be either solid or expanded vinyl which has internal air bubbles which are usually a closed-cell type of foam. Because such structures usually have a non-porous exterior or front surface or face, such structures display poor breathability and moisture vapor transmission. However, since the interior or back surface or face is porous, such materials can be used in the practice of this invention by applying the curable, thixotropic material and one or more modifier to the back face thereof.

3. Filtration Membranes

Filtration membranes contemplated for use in the practice of the present invention include microporous membranes, ultrafiltration membranes, asymmetric membranes, and the like. Suitable membrane materials include polysulfone, polyamide, polyimide, nitrocellulose, cellulose acetate, nylon and derivatives thereof. Other porous webs suitable for use in the practice of the present invention include fibers, woven and non-woven fabrics derived from natural or synthetic fibers, papers, and the like. Examples of papers are cellulose-based and glass fiber papers.

II. Curable Thixotropic Materials

In general, any curable, thixotropic material may be used to treat the webs of the present invention. Such materials are preferably polymers, more preferably silicone polymers.

A curable material is capable of undergoing a change in state, condition, and/or structure in a material, such as a curable polymer composition that is usually, but not necessarily, induced by at least one applied variable, such as time, temperature, radiation, presence and quantity in such material of a curing catalyst or curing accelerator, or the like. The term "curing" or "cured" covers partial as well as complete curing. In the occurrence of curing in any case, such as the curing of such a polymer composition that has been selectively placed into a porous flexible substrate or web, the components of such a composition may experience occurrence of one or more of complete or partial (a) polymerization, (b) cross-linking, or (c) other reaction, depending upon the nature of the composition being cured, application variables, and presumably other factors. It is to be understood that the present invention includes polymers that are not cured after application or are only partially cured after application.

The curable polymer composition is believed to be typically polymeric, (usually a mixture of co-curable polymers and oligomers), and to include a catalyst to promote the cure. The term "polymer", or "polymeric" as used herein, refers to monomers and oligomers as well as polymers and polymeric compositions, and mixtures thereof, to the extent that such compositions and mixtures are curable and shear thinnable. The polymers that can be used in the present invention may be monomers or partially polymerized polymers commonly known as oligomers, or completely polymerized polymers. The polymer may be curable, partially curable or not curable depending upon the desired physical characteristics of the final product. The polymer composition can include additives. While silicone is a preferred composition, other polymer compositions include polyurethanes, fluorosilicones, silicone-modified polyurethanes, acrylics, polytetrafluorethylene-containing materials, and the like, either alone or in combination with silicones.

As indicated above, the activity transpiring at a final step in the practice of this invention is generically referred to as curing. Conventional curing conditions known in the prior art for curing polymer compositions are generally suitable for use in the practice of this invention. Thus, temperatures in the range of about 250° F. to about 350° F. are used and times in the range of about 30 seconds to about 1 minute can be used, although longer and shorter curing times and temperatures may be used, if desired, when thermal curing is practiced. Radiation curing, as with an electron beam or ultraviolet light, can also be used. However, using platinum catalysts to accelerate the cure while using lower temperatures and shorter cure times is preferable. A curable polymer composition utilized in the practice of this invention preferably has a viscosity that is sufficient to achieve an internal coating of the web. Generally, the starting viscosity is greater than about 1000 centipoise and less than about 2,000,000 centipoise at a shear rate of 10 reciprocal seconds. It is presently most preferred that such composition have a starting viscosity in the range of about 5,000 to about 1,000,000 centipoise at 25° C. Such a composition is believed to contain less than about 1% by weight of volatile material.

Curing temperatures from about 320° F. to about 500° F., applied for times of from about two minutes to about thirty seconds (depending on the temperature and the polymer composition) are desirable. If a curing accelerator is present in the polymer, curing temperatures can be dropped down to temperatures of about 265° F. or even lower (with times remaining in the range indicated). The cure temperature is controlled to achieve the desired crosslinked state; either partial or full. The source and type of energy can also affect the placement of the polymer and additives. In place of an oven, or in combination with an oven, a source of radiation can be employed (electron beams, ultraviolet light, or the like) to accomplish curing, if desired. For example, by using a high degree of specific infrared and some convection heat energy for cure, some additives can be staged to migrate and/or bloom to the polymer surfaces.

A thixotropic material has a liquid flow behavior in which the viscosity of a liquid is reduced by shear agitation or stirring so as to allow the placement of the liquid flow to form: (a) a thin film of a polymer composition encapsulating the structural elements (i.e., the fibers or filaments) making up the web leaving at least some of the interstitial spaces open; (b) an internal layer of a polymer composition; or (c) some combination of the foregoing. It is theorized to be caused by the breakdown of some loosely knit structure in the starting liquid that is built up during a period of rest (storage) and that is broken down during a period of suitable applied stress.

Energy sources contemplated for use in the practice of the present invention include subjecting the curable, thixotropic material to shearing conditions ("treating materials"). The term "shear thinning," in its broadest sense, means the lowering of the viscosity of a material by the application of energy thereto. For example, the shearing conditions may be provided by passing the treating material and web in contact with one or more blades at a fixed orientation with respect to the blades. The blades may be either rigid or flexible to accommodate a greater variety of web materials. For example, a more rigid blade may be used if the web is soft and flexible. Similarly, a flexible blade may be used if the web is hard and rigid.

Alternatively, the energy may be provided by passing the treating materials and web through rollers at a controllable pressure. Other sources of energy contemplated for use in the practice of the present invention include thermal energy, ultrasonic energy, electron beam, microwave, and electromagnetic radiation. The pressured application of the polymer is sensitive to the viscosity of the polymer composition. Temperature affects the polymer composition by reducing or altering its viscosity, although at above a certain temperature the polymer will begin to cure. Shear-induced temperature changes occurring during application or during subsequent shear processing of the polymer can affect viscosity. The chemical composition of the polymer also plays a role in the treating process and effects in the treatment of web structural elements (including fibers) and the regulation of the filling of interstices and open cell voids.

Various other and further features, embodiments, and the like which are associated with the present invention will become apparent and better understood to those skilled in the art from the present description considered in conjunction with the accompanying drawings wherein presently preferred embodiments of the invention are illustrated by way of example. It is to be expressly understood, however, that the drawings and the associated accompanying portions of this specification are provided for purposes of illustration and description only, and are not intended as limitations on the invention.

BRIEF DESCRIPTION OF THE DRAWINGS

The figures are scanning electron microscopy (SEM) photomicrographs of webs of the present invention.

DESCRIPTION OF THE PREFERRED EMBODIMENTS

Figure 1A:
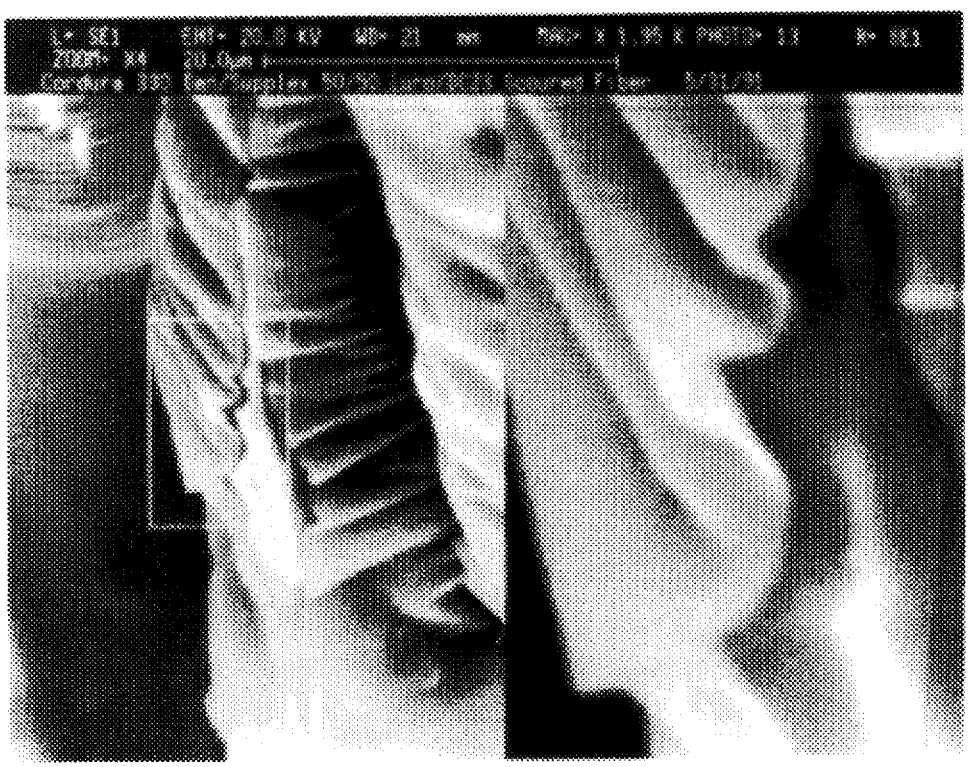
FIGS. 1a, 1b, 1c, 1d, 1e, 1f, 1g, and 1h are scanning electron microscopy (SEM) photomicrographs which depict various results in fabrics, fibers and filaments from back scatter evaluation tests.

The following description includes the best presently contemplated mode of carrying out the invention. This description is made for the purpose of illustrating the general principles of the inventions and should not be taken in a limiting sense.

The following factors effect the effective pore size of the web: (1) Thickness of the thin film encapsulating the web's structural elements and the thickness and placement of the internal layer of polymer; (2) Polymer density, structure and crosslinking orientation; and (3) Diffusion, permeation, and sorption of the polymer. Examples of preferred effective porosities are shown in Table 1 below.

TABLE 1

Physical Size Comparison

| ITEM | SIZE OR SIZE RANGE (microns) |
|---|---|
| Effective Porosity of Web | 0.025–100 |
| Viruses | |
| Foot & Mouth | 0.008–0.012 |
| Influenza | 0.070–0.080 |
| Rabies | 0.100–0.150 |
| HBV | 0.042–0.047 |
| HCV | 0.027–0.030 |
| HIV | 0.080–0.110 |
| φXI74 | 0.025–0.027 |
| Ebola | about 0.970 |
| Bacteria | |
| E. Coli | 0.50–3.0 |
| S. Aureus | 0.80–1.0 |
| Spirillum Volutons | 13–14 |
| Gas Molecules | |
| Water Vapor | 0.002 |

The table below provides an aproximate measure of the variables required to adjust the effective pore size of a web treated in accordance with the present invention. The following variables are kept constant for all of the ranges in the chart below: (1) number of blades is two; (2) entry nip pressure is 50 p.s.i.; (3) static control is on; (4) blade thickness is 0.33 inches for blade one and 0.50 inches for blade two; (5) polymer is General Electric 6108 A:B (1:1) Silicone Polymer; (6) accelerators and inhibitors are 0.01% by wt. platinum accelerators added to polymer; (7) no additives are used except for a fluorochemical pre-treatment of the web; (8) oven cure temperature is 350 degrees F.; (9) oven cure dwell time is 25 seconds; (10) ambient polymer temperature is 78 degress F.; (11) humidity is 65%; (12) web is moderately deformed; (13) airborne contaminants are moderate; (14) blade edge conditions are root mean square 8 surfaces; and (15) the initial rheology and viscosity of the polymers is 200,000 cps.

in relation to horizontal reference point, (4) blade pressure against moving web, (5) angle of exit of web from each blade, (6) web speed, (7) number of blades, (8) the pressure of the leading nip roles, (9) the pressure of the trailing nip roles, (10) static control, (11) thickness of each blade, (12) bevel on each blade, (13) oven cure temperature, (14) oven cured dwell time, (15) blade temperature and blade surfaces and edge conditions and blade finish. Other variables include: (16) the polymer blend, (17) the starting viscosity, (18) polymer composition, (19) accelerators added to the polymer composition, (20) additives added to the polymer composition, (21) the type of web used, (22) ambient temperature, (23) humidity, (24) airborne contaminants, (25) lint on web, (26) pre-treatment of web, (27) sub-web surface temperature, and (28) web moisture content.

1. Web tension

Changing the tension of the web results in changes internally in the web, such as the position of the internal layer of the web, as well as how much or how little fiber encapsulation occurs, and the thickness of the film encapsulating the individual fibers or filaments. Tension causes the web to distort. This distortion facilitates the entrance of the polymer composition into the web by creating a double or dual shear thinning.

At the leading edge of the blade, the web is stretched longitudinally and the polymer is simultaneously and dynamically shear thinned, placed into the web, and partially extracted from the web, thereby leaving encapsulated fibers and filaments and/or an internal layer. As the web passes the leading edge of the blade, the elastic recovery forces of the web combined with the relaxation or elastic recovery of the fibers and filaments causes fiber encapsulation and the surface chemistry modification (or bloom). It is believed that this occurs by the popping apart of the individual fibers and filaments. The fibers and filaments either pull the polymer from the interstitial spaces or the rheology of the polymer attracts it to the fibers and filaments or some combination of the two. The end result is that the polymer in the interstitial spaces moves to the fibers and filaments as they move or snap apart, thereby creating encapsulated fibers and filaments. A wider blade results in a thicker internal layer of polymer. Further, the dynamics of stretch and relaxation of

TABLE 2

| Effective Pore Size Range | Web Tension | Fabric Entry Angle | Fabric Exit Angle | Blade Height | Blade Angle | Web Speed | Exit Nip Press | Substrate Type |
|---|---|---|---|---|---|---|---|---|
| Small Range Approximately 25 to 110 Nanometers | 400 lbs | 29° | 26° | 6 inch. below plane of blade rolls | Blade 1.90° 2.90° | 25 yards per minute | 100 psi | Polyester |
| Medium Range Approximately 0.5 to 3 Microns | 350 lbs | 32° | 27° | 4 to 6 inch. below plane of blade rolls | Blade 1.90° 2.90° | 35 yards per minute | 80 psi | Polyester |
| Large Range Approximately 3 to 100 Microns | 300 lbs | 34° | 26° | 3 to 5 inch. below plane of blade rolls | Blade 1.85° 2.90° | 35 yards per minute | 70 psi | Nylon |

I. Thickness of the Thin Film Encapsulating the Web's Structural Elements and the Thickness and Placement of the Internal Layer of Polymer Factors and variables affecting the thickness of the thin film encapsulation and the thin film internal layer include: (1) web tension (both overall web tension as well as the web tension immediately before and after each individual blade); (2) angle of entry of the web into its blade, (3) blade angle the fibers provides for an even distribution of energy necessary for the thin film encapsulation of the polymer composition over the fibers.

An increase in web tension causes less polymer to be applied to the web, and also, more of what is applied to be extracted from the web. Web tension occurs between the entrance pull stand and the exit pull stand. The primary tension is a result of the differential rate between the driven entrance pull stand and the driven exit pull stand whereby the exit pull stand is driven at a rate faster than the entrance pull stand. Other factors which effect tension are (1) the blade roll diameter, (2) the vertical depth of the blade(s), (3) the durometer of the entrance pull stand roll and rubber roll of the exit pull stand, and (4) the friction as the web passes under the blade(s). The larger the blade roll diameter, the higher the tension of the web. If the drive rate of the web remains constant, then increasing the depth of the blade into the web creates a greater micro tension condition under the blade. Similarly, decreasing the depth into the web decreases the micro tension under the blade. The lower the durometer of the entrance pull stand roll and rubber roll of the exit pull stand, the larger the footprint or contact area between the rolls. A larger footprint produces more surface friction, thereby limiting web slippage and increasing the potential for web tension. Likewise, web slippage can be effected by changing the surface texture of the rolls, i.e., a smooth roll will allow greater slippage than a highly contrasting or rough surface texture. Increasing friction, as the fabric passes under the blade(s), also produces tension. Friction is a function of the surface area of the bottom of the blade(s). Increasing the surface area increases the friction which increases the tension.

Preferred web tensions are from 200–500 lbs, more preferably 300–400 lbs. Using standard control settings, effective pore size of approximately 25–110 nanometers can be achieved with a web tension of 400 lb plus or minus 5–10 lbs; 0.5 to 3 microns with approximately 350 lbs; and 3 to 100 microns with about 300 lbs. Standard control settings are presented below in example 4.

2. Angle of entry of the web into its blade

The angle of entry of web in contact with the blade(s) can be varied by blade roll height, blade roll diameter, blade angle, distance between prior blade roll(s) and blade(s), and height of the blades. Increasing the blade roll height and blade roll diameter increases the angle of exit of web from contact with the blade. Rotating the blade angle clockwise from the perpendicular, with the web running left to right, increases the angle of entry of web in contact with the blade(s). Likewise, rotating the blade angle counterclockwise from the perpendicular, with the web running left to right, decreases the entry angle. Decreasing the distance between the roll before the blade and the blade decreases the contact angle. Increasing the downward depth of the blade(s) into the web decreases the contact angle with the blade(s).

Preferred angles of entry are 25–40 degrees. Examples of angles that can be used under standard operating parameters to achieve various porosities are listed in Table 2. These angles can preferably be varied approximately 0.5–2 degrees.

3. Blade angle in relation to horizontal reference point

The angle of the blade(s) is completely changeable and fully rotational to 360. The fully rotational axis provides an opportunity for more than one blade per rotational axis. Therefore, a second blade having a different thickness, bevel, shape, resonance, texture, or material can be mounted. Ideally, apparatus employed in the practice of the present invention contains two or three blades per blade mount.

The apparatus used for orienting one or more modifiers on and within a web has facilities for rotating the angle of each blade ±90° from the vertical. In order to vary the shear and placement forces of the blade against the web, polymer and additives, adjustment facilities are provided for moving the blade vertically up and down and moving the blade forward and backward horizontally. All three axes are important for creating the desired control which causes additives and/or modifiers to orient on and within (a) thin film encapsulation of the individual fibers and filaments (b) the controlled placement of the internal coating, and (c) some combination of (a) and (b). The lateral placement of each blade relative to the other is also important and facilities are provided for allowing lateral movement of each blade toward and away from each other. The lateral placement of each blade controls the micro tension and elastic vibration of the web between the preceding roll and the blade, thereby controlling the web after the immediate exit of the web from the blade and controlling the Coanda Effect, as described in U.S. Pat. No. 4,539,930, so that controlled placement of the internal layer takes place.

4. Blade pressure against moving web

The blade height or blade pressure applied against a web can be obtained through the vertical positioning of the blade(s) in the blade mount. The greater the downward depth of the blade(s), the greater the pressure. Blade pressure against the web is also accomplished through the tension applied to the web, as described above.

Preferred blade heights are 2–7 inches below the plane of the blade rolls. The numbers shown in Table 2 for controlling the effective pore size can be varied 0.5 to 1 inch as other factors are varied from the standard operating conditions.

5. Angle of exit of web from each blade

The same line components that affect the angle of entry of web in contact with the blade(s), also affect the angle of exit of web from contact with the blade(s). Any changes in blade roll(s) vertical height, diameter, or distance away from the blade, affects the exit angle of the web. If the angle of the blade is rotated clockwise as described above, the entry angle of the web increases, thus decreasing the exit angle.

Preferred angles are approximately 25–28 degrees, more preferably 26–27 degrees.

6. Web speed

Web speed is proportional to the variable speed of the motor which drives the entrance and exit nip stands. Web speed can effect the physics of the polymers as the web passes under the blades.

Preferred web speeds are 20–40 yards per minute, more preferably 25–35 yards per minute.

7. Number of blades

The number of blades can vary. Generally, more than one blade is required. The polymer is first applied onto the web prior to the first blade but can also be applied prior to additional blade positions. At each blade, a rolling bead of polymer can exist at the interface of the blade and the web (entry angle) Basically, a high viscosity polymer is applied and through the process of shear thinning, the viscosity is greatly decreased, allowing the polymer to enter into the interstitial spaces of the web. Any blade(s) after the first blade, serves to further control the polymer rheology and viscosity and continue the controlled placement of the polymer into the web. This is accomplished by controllably removing excess polymer to obtain an even distribution of polymer to any area, or a combination of the three areas of a) the thin film encapsulation of the individual fibers and filaments, b) the controlled placement of the internal layer, and c) the controlled placement of the additives in a) and b).

By having a number of shear thinning blades, a multiple shear thinning effect is created, which changes the final construct of the polymer and the (a) thin film encapsulation of the individual fibers and filaments, (b) controlled placement of the internal coating, and (c) controlled placement of the additives in (a) and (b). It is understood that the first shear thinning causes viscoelastic deformation of the polymer composition which, due to its memory, tends to return to a certain level. With each multiple shear thinning, the level to which the polymer starts at that shear point and returns is changed. This is called thixotropic looping or plateauing.

8. Pressure of the leading nip rolls

The entrance pull stand is a driven roll proportionally driven at a predetermined rate slower than the exit pull stand. The entrance and exit pull stands are adjustable from about 100 pounds of force to 5 or more tons of force. The bottom rolls of both the entrance and exit pull stands have micro-positioning capability to provide for gap adjustment and alignment. The composition of the top roll of the entrance and exit pull stands is chosen based on the durometer of the urethane or rubber. The top roll of the exit pull stand preferably utilizes a Teflon sleeve which will not react with the polymers used in the process. The bottom roll of the exit pull stand is preferably chrome plated or highly polished steel to reduce the impression into the preplaced polymer in the web.

An additional nip stand can be added between the blades to divide the tension zone into multiple tension areas with blades in one or more of the tension areas. This enables the operator to adjust the tension at any one blade and to therefore control the placement of the additives into and onto the web by controlling the placement of the polymer composition.

Preferred pressure is about 50 p.s.i. although various other pressures are also suitable.

9. Pressure of the trailing nip rolls

Passing the treated web through the exit nip rolls pushes the fibers or structural elements of the web together. The hardness of and the material of the exit nip rolls affects the finished web. The exit nip rolls could be either two rubber rolls or two steel rolls, or one steel roll and one rubber roll, and the rubber rolls could be of different durometers. Further, the variation of the hardness of one or both nip rolls changes the contact area or footprint between the nip rolls and the web as the web passes therebetween. With a softer roll there is a larger contact area and the web is capable of retaining the controlled placement of additives and/or modifiers to orient on and within the: (a) thin film encapsulation of the individual fibers and filaments, (b) the controlled placement of the internal coating, and (c) some combination of (a) and (b). With a harder roll there is a smaller contact area which is appropriate for heavier webs.

Preferred pressures are about 60–110 p.s.i., more preferably 70–100 p.s.i.

10. Static control

The static control of the equipment is preferably turned on, although various effective pore sizes may be obtained with static control turned off.

11. Thickness of each blade

Blade thickness and shape have substantial effects on the movement of the structural elements of the web during processing and more importantly, the viscoelastic flow characteristics of the polymer in controlling the orientation of the additives and/or modifiers on and within the (a) thin film encapsulation of the individual fibers and filaments, (b) the controlled placement of the internal layer, and (c) some combination of (a) and (b).

Preferrably, there are two blades and the first blade is about 0.33 inches thich and the second blade is about 0.5 inches thick.

12. Bevel on each blade

The blade bevel can effect the entry angle of the web and effect the sharpness of the leading edge of the blade. A sharper leading edge has a greater ability to push the weave or structural elements of the web longitudinally and transversely, increasing the size of the interstitial spaces. As the web passes the leading edge of the blade, the interstitial spaces snap back or contract to their original size. The polymer viscosity is reduced and the polymer is placed into the web at the leading edge of the blade. Blade thickness and shape effects the polymers and their selected additives and the placement thereof. Preferably, the combination of the leading edge condition and the two surfaces (the front and the bottom) that meet at the leading edge are RMS 8 or better in grind and/or polish. This creates a precise leading edge; the more precise the leading edge, the more the shear thinning control.

13. Oven cure temperature

The oven cure temperature and the source and type of cure energy, are controlled for a number of reasons. The oven cure temperature is controlled to achieve the desired crosslinked state; either partial or full. The source and type of energy can also affect the placement of the polymer and additives. For example, by using a high degree of specific infrared and some convection heat energy for cure, some additives can be staged to migrate and/or bloom to the polymer surfaces.

Oven cure temperature is thermostatically controlled to a predetermined temperature for the web and polymers used. Machine runs of new webs are first tested with hand pulls to determine adhesion, cure temperature, potentials of performance values, drapability, aesthetics, etc. The effect on the web depends on the oven temperature, dwell time and curing rate of the polymer. Webs may expand slightly from the heat.

In view of the fact that between the shear thinning stations and the oven, the polymer composition may begin to set or partially cure, it may be desirable to overshear so that by the time the web reaches the curing oven, it will be at the point where it is desired that the cure occur. This over shear effect is a matter of controlling certain variables, including the force of the blades against the moving web, as well as the tension and speed of the web.

14. Oven cured dwell time

Oven cure dwell time is the duration of the web in the oven. Oven cure dwell time is determined by the speed of the oven conveyor and physical length of the oven. If the dwell time and temperature for a particular web is at maximum, then the oven conveyor speed would dictate the speed of the entire process line or the length of the oven would have to be extended in order to increase the dwell time to assure proper final curing of the web.

15. Blade temperature and blade surfaces and edge conditions and blade finish

With respect to the blades, the blade frontal and trailing edges and the finish of the surfaces that meet to make these edges, are important. A hard, smooth surface of both blade face and edges is desirable to shear thin the polymer and keep it flowing and to maximize friction or selectively create shear forces between the web, the polymer, and blade(s). For some applications, the blades should preferably remain rigid in all dimensions and have minimal resonance in order to achieve uniform web treatment. Preferred blades are RMS 8.

16. Polymer blend

There are a number of pre-qualifiers or engineered attributes of polymers that enhance control of flow and orientation of additives and/or modifiers on and within the (a) thin film encapsulation of the individual fibers and filaments, (b) the controlled placement of the internal coating, and (c) some combination of (a) and (b). Blending polymers is one way to achieve ideal flow and placement characteristics. An example of a blended polymer is where one polymer, selected for its physical properties, is mixed with another polymer that is selected for its viscosity altering properties. Many tests using different polymer blends have been done. Polymer blends vary by both chemical and physical adhesion, durability, cure dwell time required, cure temperature required, flexibility, percentage add-on required, performance requirements, and aesthetics.

17. Starting viscosity

A polymer composition having a starting viscosity in the range of greater than 1,000 centipoise but less than 2,000,000 centipoise is preferably used to produce the treated webs. If desired, additives and/or modifiers can be admixed with such a composition to adjust and improve properties of such composition or web, such as viscosity and/or rheology, combustibility, reflectivity, flexibility, conductivity, light fastness, mildew resistance, rot resistance, stain resistance, grease resistance, and the like. In general, a web treated in accordance with this invention exhibits enhanced durability. These additives are generally controlled by the engineered shear thinning polymer composition and the method and apparatus of this invention to be oriented and surface exposed on the surface of the thin film on the encapsulated fibers, or on one or both surfaces of the internal layer, or on one or both surfaces of the web, or some combination of the above.

18. Polymer composition

Various polymer compositions suitable for use in the present invention are described in detail in U.S. patent application Ser. No., unassigned, filed May 17, 1995, entitled "Internally-Coated Porous Webs With Controlled Positioning of Modifiers Therein", incorporated herein by reference in its entirety, including any drawings.

19. Accelerators added to the polymer composition

Accelerators and inhibitors which are added to polymers, generally produce three effects. An illustrative accelerator or inhibitor is a platinum catalyst, which is a cure or crosslinking enhancer. The first effect it produces is to control the time and temperature of the web as it cures. A cure or controlled crosslinking enhancer can significantly assist in controlling the drape and hand feel of the web. The second effect is to alter the cure to allow the web to reach partial cure and continue curing after leaving an initial heat zone. This second effect also assists in retaining the drape and hand feel of the web. The third effect of inhibitors is to achieve a semi-cure for later staging of the cure.

20. Additives added to the polymer composition

Various additives suitable for use in the present invention are described in detail in U.S. patent application Ser. No. unassigned, filed May 17, 1995, entitled "Internally-Coated Porous Webs With Controlled Positioning of Modifiers Therein", incorporated herein by reference in its entirety, including any drawings.

21. Type of web used

The physical construction and chemistry of the web is critical. The amount of control over the rheology of the polymer and the tension on the web are dependent on the physical construction and chemistry of the web and chemistry of the composition(s) applied to the web. The web selected for use in the practice of the present invention must have physical characteristics that are compatible with the flow characteristics of the polymer to achieve the desired results.

22. Ambient temperature

The ambient polymer temperature refers to the starting or first staging point to controlling the viscosity and rheology. The process head can control the ambient polymer temperature through temperature controlled polymer delivery and controlled blade temperatures.

23. Humidity

Humidity can sometimes inhibit or accelerate curing of the polymer. Therefore, humidity should be monitored and, in some conditions, controlled.

24. Pre-treatment of web

Various pre-treatment procedures suitable for use in the present invention are described in detail in U.S. patent application Ser. No. unassigned, filed May 17, 1995, entitled "Internally-Coated Porous Webs With Controlled Positioning of Modifiers Therein", incorporated herein by reference in its entirety, including any drawings.

II. Polymer density, structure and crosslinking orientation

Generally, the density is considered a gauge as to the amount of free volume within a polymer. Usually a reduction in density of the polymer results in an increase in permeability. This theory can be extrapolated and combined with observations of thin film phenomenon. At film thickness of 125 nanometers or less, the configuration or final polymer construct is altered to be less dense than at thicker films or original design requirement considerations. It is known in the art that the flexibility of the siloxane backbone dominates the permeation properties. The siloxane backbone allows rapid chain segment motion to occur in the silicone polymer.

In non-crystalline polymers, diffusion coefficients decrease approximately internally with cross link density at low to moderate levels of cross-linking. Cross-linking reduces the mobility of the polymer segments due to the combination of the small thickness of the thin films that encapsulate the structural elements and form an internal layer and the residual shear thin state of the polymer the cross-linking opportunities are reduced. This reduction in cross-linking opportunities results in greater mobility of the polymer segments which increases the diffusion coefficients causing greater overall permeability.

In conventional web treatments, cross-linking agents may be added to make the web elastomeric, rigid and rubbery due to the lower permeability of the polymer composition. The present invention is based in part on the surprising discovery that when the viscosity of the polymer is suddenly reduced prior to curing that extremely thin films form within the web. The polymer is immediately cured and results in a permeable web that retains most of its original untreated feel. Thus, more cross-linking agents may be used in the present invention than in conventional procedures in view of the reduced number of cross linking opportunities availlable to the shear thinned polymer. In view of the above it can be seen that the present invention provides webs with elevated levels of cross linking agents without reducing the permeability of the web.

III. Diffusion, permeation, and sorption of the polymer

The process of permeation through non-porous polymers is generally explained in terms of the solution diffusion model. This model postulates that the permeation of a gas through a polymer film occurs in three stages: (1) sorption of the gas on to the polymer, (2) diffusion through the polymer and (3) desorption from the opposite face. Thus it can be seen that the permeability by a combination of the diffusivity of the gas dissolved in the polymer and its concentration gradient, which in turn is proportional to the gas solubility in the polymer. For example, it can be shown that P=DS whereP is the permeability constant, D is a diffusion constant and S is a solubilit coefficient.

1. Sorption

The term 'sorption' is generally used to describe the initial penetration and dispersal of permeant molecules into the polymer matrix. The term includes adsorption, absorption, incorporation into microvoids and cluster formation. The permeant may undergo several modes of sorption simultaneously in the same polymer. In addition, the distribution of permeant between the different sorption modes may change with concentration, temperature and swelling of the matrix as well as with time.

The extent to which permeant molecules are sorbed and their mode of sorption in a polymer depend upon the enthalpy and entropy of permeant/polymer mixing, i.e. upon the activity of the permeant within the polymer at equilibrium. Sorption behavior has been classified on the basis of the relative strengths of the interactions between the permeant molecules and the polymer or between the permeant molecules themselves within the polymer.

2. Diffusion

For simple gases, where interactions with polymers are weak, the diffusivity D is independent of permeant gas concentration. However, in instances where the permeant, e.g. an organic vapour, interacts strongly with the polymer, D becomes dependent on permeant concentration and on other factors such as permeant size and shape, time and temperature.

Molecular models of diffusion are based on specific relative motions of permeant molecules and polymer chains and introduce relevant structural, energy, volume and pressure parameters. The energy for diffusion, $ED$, is postulated to arise from the need to separate the polymer matrix sufficiently to allow the permeant molecule to make a unit diffusional jump. While the resulting equations describe the variation of ED with temperature and permeant size, a number of adjustable parameters with no closely defined physical meaning are necessary. Further adjustable parameters are called for, in order to extend the temperature range of the models through Tg, and the calculations become increasingly complex.

3. Permeation

The diffusivity D is a kinetic parameter and is related to polymer-segment mobility, while the solubility coefficient S is a thermodynamic parameter which is dependent upon the strength of the interactions in the polymer/permeant mixture. Hence D and S are affected in different ways by variables such as permeant concentration and type. However, since the permeation behaviour depends on both D and S, it is clear that the permeation coefficient P will vary in a more complex fashion. Generally, variations in D can be very large, up to ten orders of magnitude, while those for S tend to be much smaller, up to three orders of magnitude. Consequently, variations in D tend to dominate the permeability, but as D is greatly affected by S it is wrong to underestimate the importance of S. Since diffusion requires conformational rearrangement of segments within a polymer chain, the behaviour is similar to that which affects the rheological and mechanical properties of the solid polymer in the presence of a permeant. While viscoelastic motions require considerable cooperative chain motions throughout the polymer, permeation behavior only requires relatively local coordination of segmented motions. Consequently, the time frame for the two processes is quite different.

Factors affecting permeation include permeant size and shape, polymer molecular weight, function groups, density and polymer structure, and crosslinking, orientation and crystallinity.

An increase in size in a series of chemically similar permeants generally leads to an increase in their solubility coefficients due to their increased boiling points, but will also lead to a decrease in their diffusion coefficients due to the increased activation energy needed for diffusion. The overall effect of these opposing trends is that the permeability generally decreases with increasing permeant size, since for many polymer/permeant pairs the sorption coeffcient will only increase by perhaps a factor of ten while the diffusion coefficient can vary by ten orders of magnitude, as previously described.

Permeant shape has a noticeable effect on permeability. For instance, flattened or elongated molecules have higher diffusion coefficients than spherical molecules of equal molecular volume. A similar correlation for the dependence of solubility coefficient on shape has been found. Generally, permeant size and shape effects are much more marked in glassy than in rubbery polymers. This arises from the differences in the permeant/polymer mixing processes. In rubbery polymers, energy is required to generate sites for the permeant molecules to occupy but, since increasing permeant size tends to increase the heat of sorption, it follows that larger permeant molecules will be readily sorbed leading to enhanced plasticization of the polymer chains. Consequently, while smaller permeants will have a greater diffusion coefficient, the polymer will be less plasticized, whereas the lower diffusion coefficient of the larger permeants will be compensated for by the higher degree of sorption. The overall effect is to minimize the difference in the permeation coefficient for large and small permeants. In glassy polymers, however, the permeation behaviour is governed by the availability of preexisting sites or 'holes' as determined by the excess free volume of the system. It has been suggested that these 'holes' have a size distribution and that, depending upon the conditions of formation of the glassy polymer, there are fewer sites available for the larger permeant molecules than for the smaller ones.

As polymer molecular weight increases, the number of chain ends decreases. The chain ends represent a discontinuity and may form sites for permeant molecules to be sorbed into glassy polymers. However, in other systems, molecular weight has been found to have no influence on the transport of liquid permeants.

The permeability of permeants which interact weakly with functional groups present in a polymer can be expected to decrease as the cohesive energy of the polymer increases. Functional groups which have specific interactions with a permeant act to increase its solubility in the polymer. This leads to plasticization and hence enhanced permeability. For instance, the very low permeability of poly(vinyl alcohol) to oxygen only applies when the polymer is perfectly dry. Sorption of water vapor plasticizes the polymer by breaking up the strong hydrogen-bonding between the polymer chains and results in a very much higher permeability. Similarly, removal of a functional group which strongly interacts with a permeant from a polymer will reduce its permeability to that permeant.

Density may be regarded as a guide to the amount of free volume within a polymer. Generally, a reduction in density in a series of polymers results in an increase in permeability. However, there are three polymers which do not fit well in this model. While it could be argued that the small differences might be due to experimental error, much more serious difficulties arise when one includes the appropriate data for the permeability of helium through butyl rubber. Butyl rubber is less permeable to helium than poly(phenylene oxide) (PPO), but it is well above its Tg (−76° C.), whereas the Tg of PPO is 220° C. Since the solubility of helium in both polymers is low, swelling effects cannot be invoked to explain this apparent anomaly. In general terms the low permeability of buyyl rubber is due to the sluggish segmental motion of the polymer chains caused by the steric hindrance of the two pendant methyl groups on every other main chain carbon atom. Poly(phenylene oxide), on the other hand, consists of chains of rigid aromatic groups which, while packed quite closely together (accounting for the higher density), are unable to move relative to one another. Consequently, permeation can occur in a relatively unhindered fashion through the microvoids which will exist due to the polymer being below its Tg.

In non-crystalline poymers, diffusion coeffients decrease approximately linearly with crosslink density at low to moderate levels of crosslinking. For instance, the diffusion coefficient of nitrogen in natural rubber is reduced tenfold on crosslinking the rubber with 11% sulfur. Generally, the solubility coefficient is relatively unaffected except at high degrees of crosslinking or when the permeant swells the polymer significantly. However, crosslinking reduces the mobility of polymer segments and tends to make the diffusivity more dependent on the size and shape of the permeant molecules and on the permeant concentration.

In crystalline polymers, the crystalline areas act as impermeable barriers to permeating molecules and have the same effect as inert fillers. i.e. they force the permeant molecules to diffuse along longer path lengths. Permeant solubility is proportional to the product of the amorphous volume fraction ØA and the solubility S of the permeant in the amorphous phase. The thermal history of a crystallizable polymer can profoundly affect the permeation properties, since this can affect the number and size of crystallites present.

Orientation of the poymer may also influence the permeation properties However, the overall effect is highly dependent upon crystallinity. For example, deformation of elastomers has little effect on permeability until crystallization effects occur. At high degrees of orientation, time-dependent effects on permeability occur in both glassy and semi-crystalline polymers. These effects have been related to the relaxation recovery of strain-induced areas of free volume generated during orientation.

Theory of Invention

The following text concerns the theory of the invention as it is now understood; however, there is no intent herein to be bound by such theory.

The presently preferred polymer composition used in the treatment of webs by this invention is a non-Newtonian liquid exhibiting thixotropic, pseudoplastic behavior. Such a liquid is temporarily lowered in viscosity by high pressure shear forces.

One aspect of the invention is a recognition that when high forces or sufficient energy are applied to curable polymer compositions, the viscosities of these materials can be greatly reduced. When the viscosity is repeatedly reduced, the result is one of thixotropically looping or massaging the viscosity rheology crosslink opportunities and overall orientation of one or more additives and/or modifiers on and/or within the (a) thin film encapsulation of the individual fibers and filaments, (b) the controlled placement of the internal coating, and (c) some combination of (a) and (b). Conversely, when subjected to curing, the same liquid composition sets to a solid form which can have a consistency comparable to that of a hard elastomeric rubber. The internal and external rheological control of polymer materials achieved by the present invention is believed to be of an extreme level, even for thixotropies. When subjected to shear force, the polymer composition is shear thinned and can flow more readily, perhaps comparably, for illustrative purposes, to water.

The invention preferably employs a combination of: (i) mechanical pressure to shear thin and place a polymer composition into a porous web; (ii) an optional porous web pretreatment with a water repellent chemical, such as a fluorochemical, which is theorized to reduce the surface tension characteristics of the web and create a favorable surface contact angle between the polymer composition and the treated web which subsequently allows, under pressure and shear force exerted upon an applied polymer composition, the production and creation of an internal coating or layer which envelopes fibers or lines cell walls in a localized region within the web as a result of polymer flow in the web or which encapsulates the fibers within the web; and (iii) a polymer composition preferably having favorable rheological and viscosity properties which responds to such working pressures and forces, and is controllably placed into, and distributed in a web. This combination produces a web having the capability for a high degree of performance. This product is achieved through pressure controlled placement and applied shear forces brought to bear upon a web so as to cause controlled movement and flow of a polymer composition and one or more additives and/or modifiers into and through a web. Preferably, repeated compressive applications of pressure or successive applications of localized shear forces upon the polymer in the web are employed.

By the preferred use of such combination, a relationship is established between the respective surface tensions of the polymer and the web, creating a specific contact angle. The polymer responds to a water repellent fluorochemical pretreatment of the substrate so as to permit enhanced flow characteristics of the polymer into the web. However, the boundary or edge of the polymer is moved, preferably repeatedly, in response to applied suitable forces into the interior region of a porous web so as to cause thin films of the polymer to develop on the fiber surfaces and to be placed where desired in the web.

Thixotropic behavior is preferably built into a polymer used in the invention by either polymer selection or design or additive/filler design. For example, it now appears that thixotropic behavior can be accentuated by introducing into a polymer composition certain additives that are believed to impart enhanced thixotropy to the resulting composition. A lower viscosity at high shear rates (during application to a web) is believed to facilitate polymer flow and application to a web, whereas a polymer with high viscosity, or applied at a low shear rate (before and/or after application) actually may retard or prevent structural element (including fiber) envelopment or encapsulation.

CROSS LINKING

1. Novel Use of Cross-Linking

A surprising and unexpected result is obtained from known polymer additives with the shear thinning process described in U.S. patent application Ser. No. 08/407,191 filed Mar. 17, 1995, herein incorporated by reference in its entirety including any drawings. The cross-linking in a polymer is normally increased to make the polymer more rigid. Theory states that increased cross-linking and/or density results in lower permeability of the cured polymer composition and that when such a polymer is placed on a web that the web becomes rigid. However, the present invention is based in part on the discovery that when the viscosity of the polymer is caused to drop suddenly and the polymer is caused to form extremely thin films within the web and then cured immediately, that the result is that a permeable web remains and retains most of its original untreated feel.

Cross-linking is the result of two simultaneous interactions: chemical reactive sites and physical entanglements. It is beleived that by adding viscosity altering agents and sufficient energy that the polymer viscosity reduces quickly enough to form extremely thin films within the web, thereby reducing the cross-linking opportunities of the polymer composition. Thus, more cross linking agents have to be added to the polymer composition because the thin films reduce the number of cross-linking opportunities. Therefore, although more cross-linking agents and/or reactive sites designed into the polymers are added, permeability is not decreased due to reduction of cross-linking opportunities of extremely thin films. These thin films may be produced by adding viscosity altering agents and shear thinning the polymer composition.

2. Detection of Cross-Linking

A number of techniques are available to evaluate cross-linked matrices obtained via hydrosilation cross-linking. Such techniques have been used to to study cross-linking by hydro-silation. Thermal analysis techniques have been used to study cross-linking by hydro-silation, including differential scanning calorimetry (DSC) and thermomechanical analyisis (TMA). The former measures the formation of chemical cross-links and the latter measures the total number of effective cross links. Swelling measurements in hexane can be used as a further estimateof cross-link densisty. The cross-linking process has been examined in the art over a range of polymer and catalyst rations and established that the number of cross links measured mechanically was greater than those introduced by chemical cross-linking. This effect was attributed to the existence of physical chain entanglements which in some circumstances could account for up to half of the elasticilly effective cross links. The development of cross-linked matrix using rheological measurements has shown excellent agreementg between theoretical calculations of onset of gelation and rheological measurements.

The hydrosilation cross-linking system, even as a two pack formulation, has established itself as a very versatile technology capable of producing a wide range of product properties. Typical formulations would be based on a mixture of the platinum complex with a vinyl functional polymethylpolysiloxane, having vinyl functionality in the pendant and/or terminal position. For a more detailed discussion of cross linking of silicone poilymers see *Silicone Polymers*, Clarson, Stephen J., Semlyen, J. Anthony, ch 12, Prentice Hall, 1993, incorporated herein by reference in its entirety including any drawings.

3. Silicone Composition

A polymer composition useful in this invention can contain curable silicone resin, curable polyurethane, curable fluorosilicone, curable modified polyurethane silicones, curable modified silicone polyurethanes, curable acrylics, polytetrafluoroethylene, and the like, either alone or in combination with one or more compositions.

One particular type of silicone composition which is believed to be well suited for use in the controlled placement step of the method of the invention is taught in U.S. Pat. Nos. 4,472,470 and 4,500,584 and in U.S. Pat. No. 4,666,765. The contents of these patents are incorporated herein by reference. Such a composition comprises in combination:

(i) a liquid vinyl chain-terminated polysiloxane having the formula:

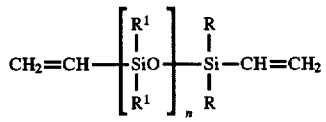

wherein R and $R^1$ are monovalent hydrocarbon radicals free of aliphatic unsaturation with at least 50 mole percent of the $R^1$ groups being methyl, and where n has a value sufficient to provide a viscosity of about 500 centipoise to about 2,000,000 centipoise at 25° C.;

(ii) a resinous organopolysiloxane copolymer comprising:
 (a) $(R^2)_3SiO_{0.5}$ units and $SiO_2$ units, or
 (b) $(R^3)_2SiO_{0.5}$ units, $(R^3)_2SiO$ units and $SiO_2$ units, or
 (c) mixtures thereof, where $R^2$ and $R^3$ are selected from the group consisting of vinyl radicals and monovalent hydrocarbon radicals free of aliphatic unsaturation, where from about 1.5 to about 10 mole percent of the silicon atoms contain silicon-bonded vinyl groups, where the ratio of monofunctional units to tetrafunctional units is from about 0.5:1 to about 1:1, and the ratios of difunctional units to tetrafunctional units ranges up to about 0.1:1;]

(iii) a platinum or platinum containing catalyst; and (iv) a liquid organohydrogenpolysiloxane having the formula:

in an amount sufficient to provide from about 0.5 to about 1.0 silicon-bonded hydrogen atoms per silicon-bonded vinyl group of above component (i) or above subcomponent (iii) of, $R_a$ is a monovalent hydrocarbon radical free of aliphatic unsaturation, and has a value of from about 1.0 to about 2.1, b has a value of from about 0.1 to about 1.0, and the sum of a and b is from about 2.0 to about 2.7, there being at least two silicon-bonded hydrogen atoms per molecule.

Optionally, such a composition can contain a finely divided inorganic filler (identified herein for convenience as component (v)).

For example, such a composition can comprise on a parts by weight basis:

(a) 100 parts of above component (i);

(b) 100—200 parts of above component (ii);

(c) a catalytically effective amount of above component (iii), which, for present illustration purposes, can range from about 0.01 to about 3 parts of component (iii), although larger and smaller amounts can be employed without departing from operability (composition curability) as those skilled in the art will appreciate;

(d) 50—100 parts of above component (iv), although larger and smaller amounts can be employed without departing from operability (curability) as those skilled in the art will appreciate; and (e) 0—50 parts of above component (v).

Embodiments of such starting composition are believed to be available commercially from various manufacturers under various trademarks and trade names.

As commercially available, such a composition is commonly in the two-package form (which are combined before use). Typically, the component (iv) above is maintained apart from the components (i) and (ii) to prevent possible gelation in storage before use, as those skilled in the art appreciate. For example, one package can comprise components (i) and (ii) which can be formulated together with at least some of component (ii) being dissolved in the component (i), along with component (iii) and some or all of component (v) (if employed), while the second package can comprise component (iv) and optionally a portion of component (v) (if employed). By adjusting the amount of component (i) and filler component (v) (if used) in the second package, the quantity of catalyst component (iii) required to produce a desired curable composition is achieved. Preferably, component (iii) and the component (iv) are not included together in the same package. As is taught, for example, in U.S. Pat. No. 3,436,366 (which is incorporated herein by reference), the distribution of the components between the two packages is preferably such that from about 0.1 to 1 part by weight of the second package is employed per part of the first package. For use, the two packages are merely mixed together in suitable fashion at the point of use. Other suitable silicone polymer compositions are disclosed in the following U.S. patents:

EXAMPLES

This invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

Examples of various internally coated fiber encapsulated liquid silicone polymer preparations, including those with one or more modifiers such as iodine, protein, pigment, dye, flattening agent, and copper and the evaluation of various fiber enapsulated fabric properties using techniques such as such as accelerated weather testing, abrasion resistance testing, breathability testing, moisture vapor transport testing, water repellancy testing, moisture penetration and rain testing and scanning electron micrographs are provided in U.S. patent application Ser. No. unassigned, filed May 17, 1995, entitled "Internally-Coated Porous Webs With Controlled Positioning of Modifiers Therein", incorporated herein by reference in its entirety, including any drawings.

The samples tested below in examples 1-3 were prepared using a simplified "hand pull" process wherein fabric is tensioned, polymer composition is applied to the tensioned fabric, and a knife is pulled across the fabric to shear thin the polymer composition, place it into the fabric, and pull the excess composition out of the fabric. Hand pulls do not always create an evenly encapsulated fabricdue to human fluctuations in applying shear forces to the polymer composition. Thus, fluctuations in MVTR may appear for samples that appear to similar polymer weight add-on percentages. Webs treated with a more complicated machinery that is better capable of uniformly controlling operating conditions are beleived to have similar or improved properties compared to those tested in examples 1-3 below.

Example 1

Viral Penetration Tests (ASTM ES 22)

This example demonstrates the ability of webs treated in accordance with this invention to prevent the penetration fo bloodborne pathogens. The treated web samples are tested according to ASTM ES 22 (1995). The pathogens of concern are the hepatitus B virus (HBV), hepatitus C virus (HCV) and the human immunodeficiency virus (HIV). Due to the infectious nature of these viruses, the assay uses a surrogate virus in conjuction with the ASTM F903 Chemical Penetration Cell apparatus. The Surrogate virus is the $\phi$X174 Bacteriophage.

Sterile test samples are placed in the Penetration Cell apparatus and challenged with the $\phi$X174 under various pressures and observed for penetration. At the conclusion of the test, the observed side of the article is rinsed with a sterile medium and then tested for the presence of $\phi$X174.

HBV, HCV, and HIV range in size from 27 nm (nanometers) to 110 nm. HCV is the smallest at 27-30 nm, HBV is 42-47 nm, and HIV is 80-110 nm. All have a spherical or icosahedral structure. The $\phi$X174 is one of the smallest known viruses at 25-27 nm and is also icosahedral or nearly spherical. The $\phi$X174 also grows rapidly and can be cultivated to reach very high titers.

The surface tension of blood and body fluids is known to be about 42-60 dynes/cm. In order to provide for similar wetting characterisitics the surface tension of the $\phi$X174 suspension is adjusted to about 40-44 dynes/cm via the use of a surfactant such as Tween®80.

The treated web samples were treated to minimize viral penetration. Thicker internal layers or encapsulating films result in better test results but lower breathability. Still, the treated webs showed some breathability when worn all day by lab technicians. The results of the test are shown in the following table

TABLE 3

Viral Penetration Test Results

| SAMPLE | CHALLENGE CONCENTRATION (plaque forming units/ml) | ES22 RESULTS |
|---|---|---|
| 4040 + GE 6108 polymer (53.3% wt. add on) | $7 \times 10^8$ | Pass |
| 4040 + LIM 6060 polymer (87.67% wt. add on) | $7 \times 10^8$ | Pass |
| $C^3$ fabric + polymer (22-35% wt. add on) | $1.5 \times 10^8$ | Pass |
| Lot #8253 (Nelson Labs) | $1.36 \times 10^8$ | Pass |

LIM stands for Liquid Injected Molding. All ES22 tests were preformed by either MO BIO Laboratories, Solana Beach, Calif. or Nelson Laboratories, Inc., Salt Lake City, Utah. Sample materials were tested in triplicate using ES22 viral barrier test as defined by ASTM. For a material to be considered a viral barrier all three of the triplicate samples must pass. $C^3$ fabric is 100% polyester with carbon fibers to reduce static.

Example 2

Bacteria Penetration Tests (Modified ASTM ES 22)

This example demonstrates the ability of webs treated in accordance with this invention to prevent the penetration of bacteria. Bacteria is generally larger in size than viruses. A modified ASTM ES 22 test described in the previous example was used to test for bacteria penetration. The test was modified to use *Escherchia coli* (*E. col8i*) ATCC umber 25922 bacteria and a different Agar solution as the nutrient broth. The media used consisted of the following:

Nutriet Broth

| Beef Extract | 3.0 g |
|---|---|
| Pancreatic digest of gelatin | 5.9 g |
| Potassium Chloride | 5.0 g |

| | |
|---|---|
| Calcium Chloride | 0.2 g |
| Distilled water to | 1000 ml |

Adjust pH to 7.2–7.4 with 2.5N Sodium Hydroxide and sterilize (40 µl/liter).

Nutrient Broth with 0.01% Tween®80:

Same formula as above with 0.1 ml of Tween®80 and 45 µl/liter of NaOH added.

Nutrient Broth with 0.01% Tween®80:

Same formula as above with 0.1 ml of Tween®80 and 45 µl/liter of NaOH added.

i E. ColiATCC 25922 is MUG positive. it will fluoresce when grown in MacConkey Agar plate with MUG (methylumbelliferyl β-D-Galactoside). The fluoresence provided a measure of selectivity for the assay. The fabric was challenged with *E. coli* ATCC strain 25922. Following the challenge the unchallenged side was assayed for penetration of the *E. Coli*. *E. Coli* ranges in size from 0.5 to 3.0 microns. The results are shown below.

believed to be a polysiloxane but containing an undisclosed active accelerated ingredient.

Example 5

Liquid Silicone Polymer Preparation

The procedure of Example 1 was repeated with various other curable viscous liquid silicone polymer compositions commercially available. To this product system is added a substituted benzophenone and other additives, the result of which are shown in Table V. All parts are by weight.

Example 6

Internally Coated Fiber Encapsulated Interstice Filled Fabric Preparation

A complete, stepwise, application of the inventive method in the production of an encapsulated fiber fabric was as follows.

The selected base fabric was TACTEL (gold color) #612071 available from ICI Americas, Inc. through their

TABLE 4

Bacterial Penetration Test Results

| SAMPLE | CHALLENGE CONCENTRATION (plaque forming units/ml) | Vapor Permeability As Percent Of Untreated Fabric | MODIFIED ES22 RESULTS |
|---|---|---|---|
| Burlington 40/40 fabric + 23.45% wt. add on GE 6108 polymer (sample H051995-N) | $6 \times 10^8$ | 75.80% | Pass |
| Burlington 40/40 fabric + 28.11% wt. add on GE 6108 polymer (sample H051995-I) | $6 \times 10^8$ | 51.60% | Pass |

Example 3

Synthetic Blood Barrier Test

This examle demonstrates the ability of the webs treated in accordance with this invention to prevent the penetration of a blood-like fluid (synthetic blood). The treated web samples were tested according to a modified ASTM ES 21 Synthetic Blood Direct Pressure Draft Test Method (ASTM F23, 40, 04) Fabric samples of $C^3$ fabric were treated according to the practice of this invention to yield a fabric with 22–35% polymer weight add-on. The synthetic blood came from Jamar Health Products (Phil Johnson), Lot 220. The surface tension of the synthetic blood is 40 dynes/cm. According to the test procedure, synthetic blood is pressed against a fabric sample at increasing pressures at one spot until wicking of the fabric occurs. The final pressure is determined by over pressuring to create failure and then backing off at different sites until a pass occurs as per ASTM protocol F23, 40, 04 draft test method. This particular treated fabric (Sample #111193B) passed at 80 psi. No wicking occurred after one hour of elapsed time.

Example 4

Liquid Silicone Polymer Preparation 100 parts by weight of the curable liquid silicone polymer available commercially from Mobay as "Silopren LSR 2530" was mixed in a 1:1 ratio, as recommended by the manufacturer. A Hockmayer F dispersion blade at low torque and high shear was used to do the mixing. To this mixture were added 5 parts by weight of BSF "Uvinul 400" and 5/10 parts by weight Dow Corning 7127 accelerator, agent, Arthur Kahn, Inc. This fabric was 100% woven nylon. If desired, this and other fabrics may be calendered to modify surface texture. The fabric was weighed and measured. Its initial weight is 3.1 ounces per square yard. Its thickness equals 9 mils. The fabric was next washed with detergent, rinsed thoroughly, and hung to air dry. The fabric was soaked in water, wrung dry, and weighed. The water retained was equal to 0.8 g water/g fabric. The fabric was then treated with a water repellent fluorochemical, a 2% solution by weight of Zepel 7040. In order to do so the fabric must be soaked in a 2.5% solution of Zepel water-repellent chemical in distilled water. This was because:

$$\{1\text{--}g\text{--}fabric\text{--}*\text{--}(0.02)\} \text{ OVER } \{0.8\text{--}g\text{--}water\}=\text{--}0.025$$

The treated fabric was then run through a wringer and air dried. Next, the fabric was heated in an oven for 1 minute at 350°. This heating sinters the water repellent fluorochemical. The fabric with its fluorochemical residue is then run, in a vertical configuration and is described below. The fabric is run from a roll that incorporates significant braking or clutching to initiate the tension required for controlled material alignment and coating during application. The fabric web travels through a series of idler rolls ending at the application trough. As it passes the application trough, it picks up a thin coating of silicone impregnant and then moves under a shear blade that is parallel to the floor. The silicone impregnant is applied at 1.0 oz./sq. yd. and continues under a flex blade that is also parallel to the floor.

Multiple process stages of running the fabric with applied impregnant under the blades are preferably made. The multiple process stages are important, and are normally necessary. The impregnant is Mobay 2530 A/B in a 1:1 ratio and can be considered to be a viscoelastic liquid that flows only under the shear forces resulting from the pressured controlled placement. The impregnant is believed to return very substantially to its original viscous condition almost immediately upon release of the pressure. The impregnant was believed to flow a short distance within the matrix of the fabric during the short time that it was, because of pressure shearing forces, of lowered viscosity. Therefore, a number of "flows" may be usefully generated in a number of passes in order to properly distribute the impregnant in its preferred position substantially encapsulating the surfaces of the fabric's fibers.

Finally, the impregnated fabric was run through a line oven, of approximately 10 yards in length, at 4_6 yards per minute, and was cured at 325°-350° F. It then passes through a series of idler rollers and is rolled up on a take_up roll, completing the tension zone. The resultant fabric has a non_tacky thin film of silicone that was internally coated to form a fiber encapsulated, interstice-filled layer in the fabric.

Example 7

Figure 1B:
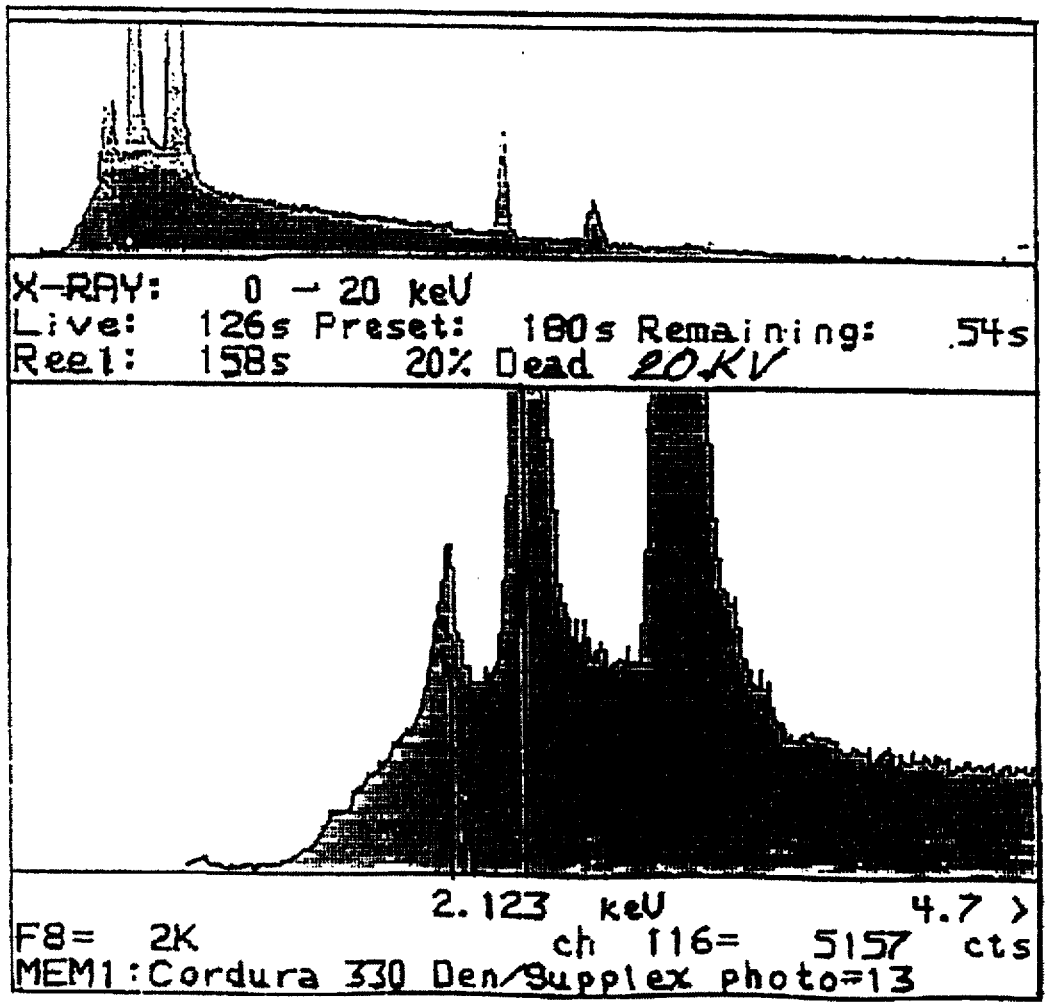

Description of Fabric Controlled Placement Through Scanning Electron Microscope (SEM) Photomicrographs FIG. 1a depicts a 330 denier cordura fiber, encapsulated with a composite polymer, magnified 1950 times. The left side of the picture is in normal scanning electron mode and the right side of the picture is magnified 10 times in secondary electron microscopy back scatter mode. The isolated rectangular box image in the middle of the left side was exposed to destructive electron beams isolated on the central opening in the center of the wrinkled formation. The wrinkled film casing represents the composite polymer (solid silicone and oxyethylated nylon) thin-film, this is a direct result of the destructive electron exposure. The image on the left side of the picture has surrounding fibers on the left and right side of the isolated fiber, which also has some wrinkled effects on the thin-film as a direct result of the destructive electron analysis. The rectangular box on the upper side of the picture was targeted for an elemental analysis. The electron beam was targeted at the rectangular box with very low current (10 KV and probe at 3.0 nA) to insure isolation of elemental signal from any other area. FIG. 1b depicts the elemental graph of the targeted region, which clearly shows the presence of the composite polymer containing si or silicon. Combined, FIGS. 3a and 3b show fiber encapsulation by the composite polymer.

Figure 1C:
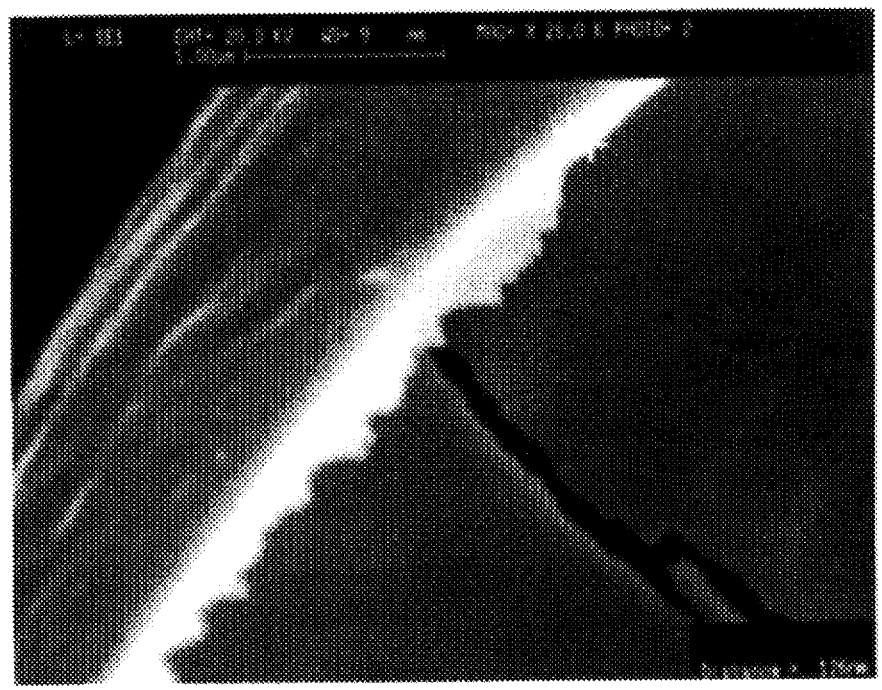

FIG. 1c depicts a cut end of a filament illustrating a thin film encapsulation in white. A crack was created in the filament with a high temperature electron beam. This crack continues under the surface of the thin film. The filament has been cut and the thin film has been stretched or elasticized by the cutting of the filament. The two arrows in the upper right corner show the thickness or distance represented by the black box in the lower right corner as 126 nm.

Figure 1D:
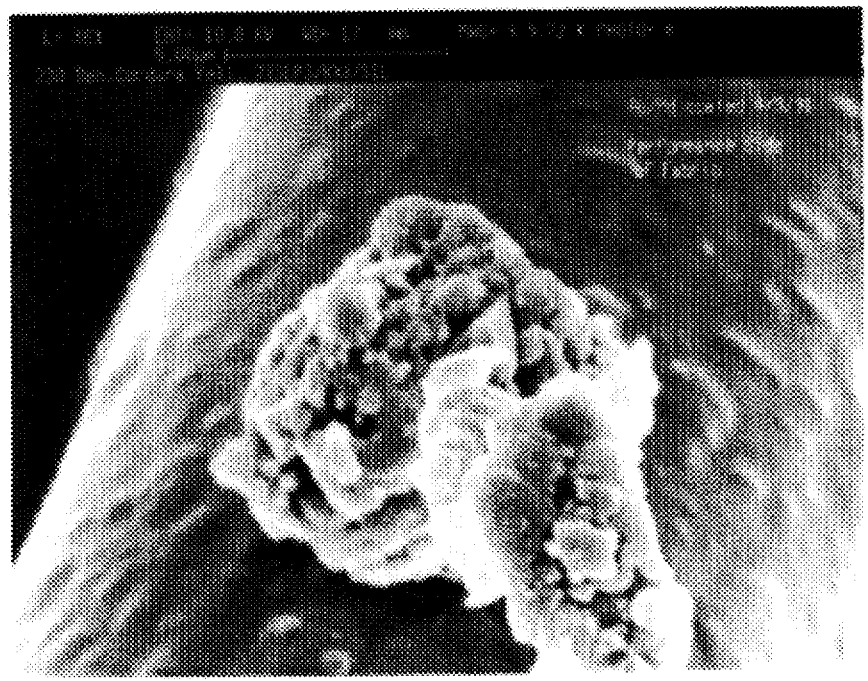

FIG. 1d depicts an isolated image on 330 Denier Cordura single filament fiber processed with the micro-finish fiber coating technology, magnified 5,720 times. The Bioengineered Comfort polymer containing engineered protein and solid silicone was used in the process with a moderate degree of shear. The image on top of the fiber is an undispensed protein polymer which clearly illustrates the presence of the protein after the micro-finish fiber coating process. The surface morphology has very small protein polymer particles encapsulated in the solid silicone polymer and is homogeneously dispersed throughout the film system on the fiber.

Figure 1E:
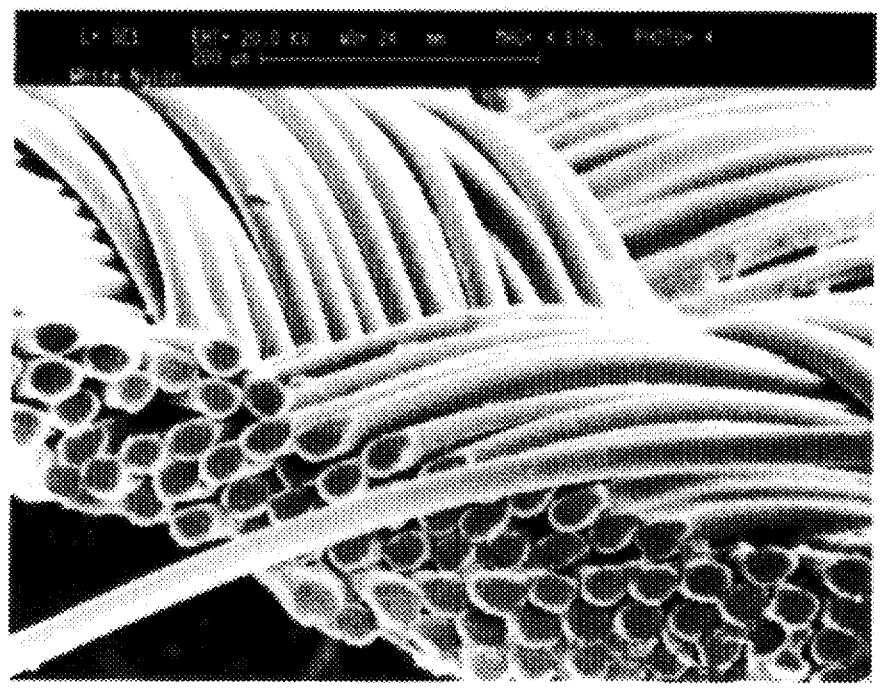

FIG. 1e is an image of a white nylon magnified 178 times. The application side is shown at the bottom left hand corner of the image. The upper portion of the image is the non-application side. At the upper right corner is the intersection of the warp and fill fiber bundles, where the polymer presence can clearly be seen on the fibers. The internal layer of polymer that creates the liquid barrier or resistant property can be seen along the bottom right corner of the picture. This internal layer is a combination of polymer filling some interstitial spaces and polymer "glueing" together the fibers and filaments of the web.

Figure 1F:
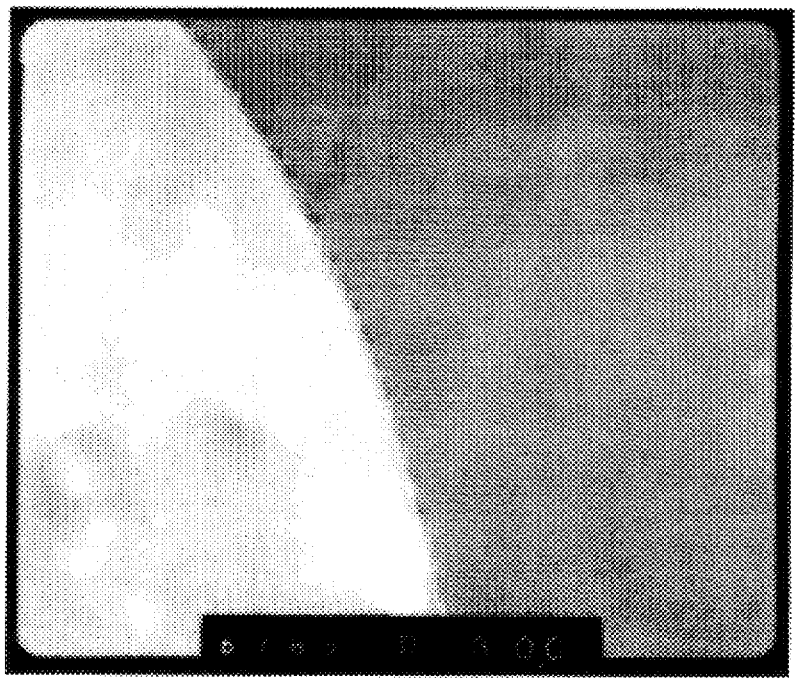

FIG. 1f is a Tunneling Electron Microscopy (TEM) image of a thin cross section of a filament encapsulated with polymer. The lighter image on the lower side of the frame is a polyester filament. The black spherical dots on the outer edge of the fiber are extremely dense processed material. In this imaging technique, the darker the image, the denser that specific material.

Figure 1G:
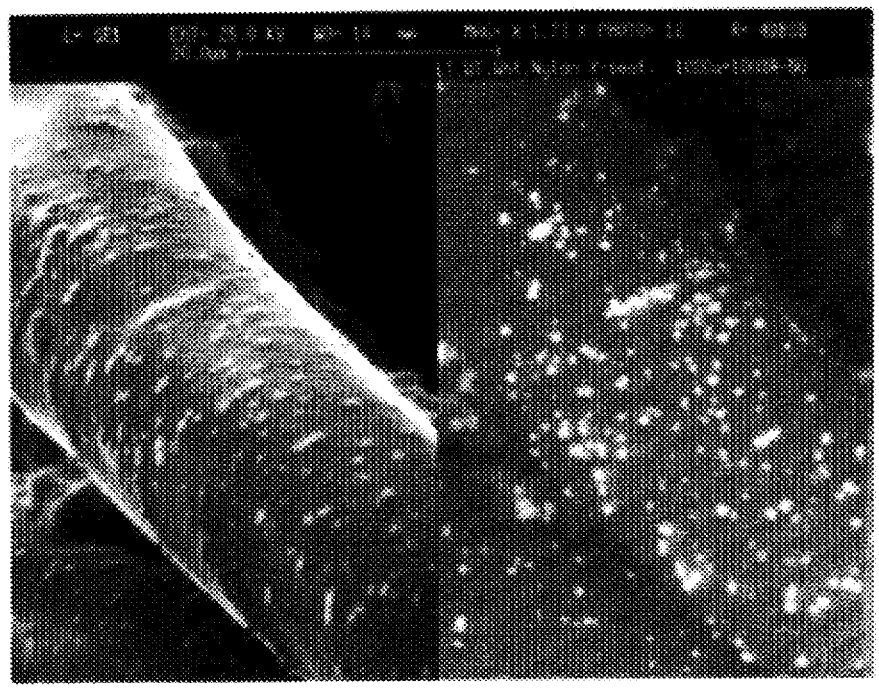

FIG. 1g depicts an individual filament shown in a split screen format. The left hand image is showing the filament with submicron metal particles dispersed in the processed film. The right hand portion of the split screen is imaging the filament with a technique known as secondary electron back scattering. The bright particles are the same particles on the same fiber as seen in the left side of the split screen. The difference is one of density, the brighter metal particles are imaging density differential over the underlying filament.

Figure 1H:
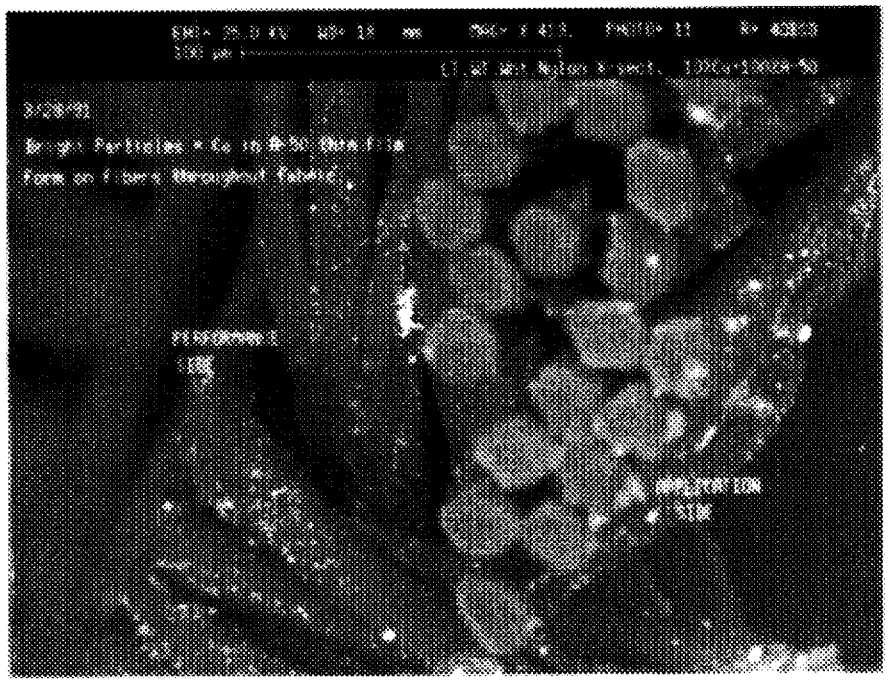
Figure 2:
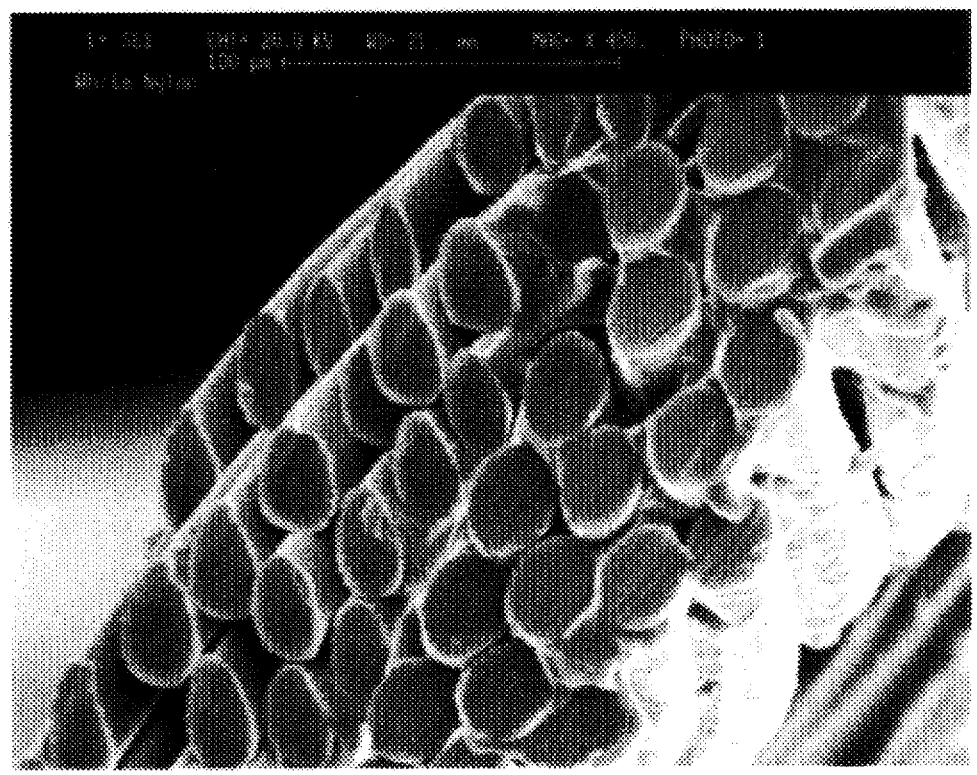
FIG. 2 is a scanning electron microscopy photomicrograph of a web of the present invention.

FIG. 1h depicts a nylon fabric magnified 419 times with bright particle tracer images and a cross sectional image of a nylon fabric. These bright particles are submicron metal particles dispersed throughout the fabric in the processed film. The addition of bright copper submicron particles in the polymer allows secondary back scatter mode to illustrate the complete encapsulation ability of the controlled placement technology. The left side of the image is the performance side of the fabric which is the non-application side of the polymer, but it is clear, with the presence of the glowing brightness of the copper submicron particles throughout the performance side of the fabric, that controlled placement technology successfully encapsulates completely around the fibers throughout the fabric structure. The other clear unique feature of the controlled placement technology is that each fiber is still independent. This differentiation allows the controlled placement technology s processed fabrics to retain exceptional hand and tactile quality, while still imparting performance characteristics. On the left side of the fabric, directly underneath the printed text "performance side", an elemental analysis was conducted. The result clearly shows a strong presence of submicron copper particles.

In the next examples that involve accelerated weathering, abrasion, water repellency, moisture penetration, and rain testing, data is provided for a Tactel fabric identified as Deva Blue. The fabric is 100% nylon, available from Arthur Kahn and identical in composition, preparation, and enveloping specification to that of the Hot Coral presented in previous examples. The moisture vapor transmission (MVTR) test was conducted in accordance with ASTM E96-B. The test measures the amount of moisture vapor passing through a fabric sample in a controlled environment during a 24 hour period. The obtained MVTR figure is expressed in grams of water/square meter of surface/24 hour day. The environmental chamber was held at 104° F. and 478 humidity.

Example 8

Breathability Testing

This test procedure followed the Modified ASTM E96-8 test. As shown by the results of this testing in the following Table, the fiber enveloped fabrics of this invention were found to have high breathability. This breathability was in excess of that needed to remove the average value of several thousand grams of perspiration generated daily by the human body. The results for the fiber enveloped fabrics of this invention were generally superior to the corresponding results measured under the same conditions for prior art treated fabrics, such as the Gore-Tex® brand fabric.

Breathability of a fabric sample was determined by accurately weighing the amount of water passing through such fabric sample under carefully controlled temperature and relative humidity conditions in an environmental chamber. The water weight loss from a cup whose mouth is sealed with a fabric sample was expressed as grams of water vapor per square meter of fabric per 24 hour day.

In an attempt to more realistically simulate what is actually occurring inside the apparel during exercise, a specially designed test was performed to measure outward water vapor transport (MVTR) in a "Bellows" effect. The test simulates the high volumes of moisture and air that mix within a garment that pass outward through it as air is drawn in resultant from activity. The enveloped fabrics of this invention were found to provide increased performance at a higher activity, or air exchange level than is achievable with corresponding untreated fabrics.

The "Bellows" MVTR breathability test was run inside of a controlled temperature/humidity chamber similar to the foregoing cup test. However, instead of a standard cup, each fabric sample was sealed over the open top of a special cup which was provided with an air inlet aperture in its bottom, thereby allowing air to be bubbled up through the sealed container at a controlled rate. A check valve at the air inlet operation prevents backup or loss of water from the container. The air bubbles passed upwardly through the water and out through the fabric sample mounted sealingly across the cup top along with the water vapor. Table VI illustrates some representation results obtained.

TABLE 5

Illustrative Silicone Resin Composition

| EX. NO. | STARTING SILICONE RESIN | MIXTURE RATIO OF PACKAGED COMPONENTS[1] | SUBSTITUTED BENZOPHENONE NAME | PARTS | OTHER ADDITIVES NAME | PARTS |
|---|---|---|---|---|---|---|
| 1 | Silopren® LSR 2530 | 1:1 | Uvinul 400 | 5 | 7127 Accelerator | 5/10 |
| 2 | Silastic® 595 LSR | 1:1 | Uvinul 400 | 5 | Syl-Off® 7611[2] | 50 |
| 3 | SLE 5100 Liquid BC-10 | 10:1 1:1 | Uvinul 400 | 5 | Sylox® 2[3] | 8 |
| 4 | Silopren® LSR 2530 | 1:1 | Uvinul 400 | 5 | Hydral® 710[4] | 10 |
| 5 | Silopren® LSR 2530 | 1:1 | Uvinul 400 | 5 | Silopren® LSR Z3042[5] | 1 |
| 6 | SLE 5500 | 10:1 | Uvinul 400 | 5 | | |
| 7 | Silopren® LSR 2540 | 1:1 | Uvinul 400 | 5 | | |
| 8 | SLE 5300 | 10:1 | Uvinul 400 | 5 | | |
| 9 | SLE 5106 | 10:1 | Uvinul 400 | 5 | | |
| 10 | Silopren® LSR 2530 | 1:1 | Uvinul 400 | 5 | Flattening Agent OK412 ®[6] | 4 |
| 11 | Silopren® LSR 2530 | 1:1 | Uvinul 400 | 5 | Nalco[5] ISJ-612 Colloidal Silica[7] | 50 |
| 12 | Silopren® LSR 2530 | 1:1 | Uvinul 400 | 5 | Nalco® ISJ-614 Colloidal Alumina[8] | |
| 13 | Silastic® 595 LSR | 1:1 | Uvinul 400 | 5 | 200 Fluid[7] | 7 |
| 14 | Silopren® LSR 2530 | 1:1 | Uvinul 400 | 5 | | |
| 15 | Silastic® 595 LSR | 1:1 | Uvinul 400 | 5 | Zepel® 7040[10] | 3 |
| 16 | Silastic® 595 LSR | 1:1 | Uvinul 400 | 5 | Zonyl® UR[11] | 1/10 |
| 17 | Silastic® 595 LSR | 1:1 | Uvinul 400 | 5 | Zonyl® FSN-100[12] | 1/10 |
| 18 | Silopren® LSR 2530 | 1:1 | Uvinul 400 | 5 | DLX-600 ®[13] | 5 |
| 19 | Silopren® LSR 2530 | 1:1 | Uvinul 400 | 5 | TE-3608 ®[14] | 5 |
| 20 | Wacker LR 6289 | 1:1 | None | — | Wacker Pt. Catalyst OL | 1 wt. % |
| 21 | Wacker LR 6289 | 1:1 | None | — | Pt. Cat. OL & HF86 Adhesion Promotor | 1 wt. % each |

TABLE 5-continued

Illustrative Silicone Resin Composition

| EX. NO. | STARTING SILICONE RESIN | MIXTURE RATIO OF PACKAGED COMPONENTS[1] | SUBSTITUTED BENZOPHENONE NAME | PARTS | OTHER ADDITIVES NAME | PARTS |
|---|---|---|---|---|---|---|
| 22 | Trial GE 2926-014 | 1:1 | None | — | Ge 88257 Pt. Catalyst | 0.1 wt. % |
| 23 | GE 6108 | 1:1 | None | — | GE 88257 Pt. Catalyst | 0.1 wt. % |

Table 5 Footnotes:
[1] Ratio listed is that recommended by the manufacturer.
[2] Syl-off ® (registered trademark of Dow Corning) is a crosslinker.
[3] Sylox ® 2 (registered trademark of W.R. Grace Co.) is a synthetic amorphous silica.
[4] Hydral ® 710 (registered trademark of Alcoa) is hydrated aluminum oxide.
[5] Silopren ® LSR Z/3042 (registered trademark of Mobay) is a silicone primer (bonding agent) mixture.
[6] Flattening Agent OK412 ® (registered trademark of Degussa Corp.) is a wax coated silicon dioxide.
[7] Nalco ® ISJ-612 Colloidal Silica (registered trademark of Nalco Chemical Company) is an aqueous solution of silica and alumina.
[8] Nalco ® ISJ-614 Colloidal Alumina (registered trademark of Nalco Chemical Company) is an aqueous colloidal alumina dispersion.
[9] 200 Fluid (registered trademark of Dow Corning) is a 100 centistoke viscosity dimethylpolysiloxane.
[10] Zepel ® 7040 (registered trademark of duPont) is a nonionic fluoropolymer.
[11] Zonyl ® UR (registered trademark of duPont) is an anionic fluorosurfactant.
[12] Zonyl ® FSN-100 (registered trademark of duPont) is a nonionic fluorosurfactant.
[13] DLX-6000 ® (registered trademark of duPont) is polytetrafluoroethylene micropowder.
[14] TE-3608 ® (registered trademark of duPont) is a polytetrafluoroethylene micropowder.

TABLE VI

Moisture Vapor Transport (MVTR)

| FABRIC | MVTR[1] |
|---|---|
| Made by a Method of the Invention Enveloped fiber fabric, Hot Coral Tactel ® | 13,600 |
| Commercial Products Gore-Tex\3-Ply Fabric | 10,711 |

Table Footnote:
[1] MVTR here references moisture vapor transport through a fabric sample as measured by the "Bellows" test with air delivered to the bubbler at 2 to 4 psi air pressure, in an Environmental Chamber at 100 to 102° F. and 38–42% relative humidity. MVTR is expressed as grams of water per square meter of surface per 24 hour day.

That which is claimed is:

1. A porous, non-rigid, shear thinned silicone polymer composition having a thickness of up to 20 microns comprising:
   (I) 50 to 400 parts of a liquid vinyl chain-terminated polysiloxane having the formula:

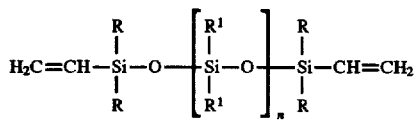

wherein R and $R^1$ are monovalent hydrocarbon radicals free of aliphatic unsaturation with at least 50 more percent of the $R^1$ groups being methyl, and wherein n is sufficient to produce a viscosity of 40,000–200,000 centipoise at 25 degrees celsius;
   (ii) 100–800 parts of a resinous organopolysiloxane copolymer comprising:
      (a) $(R^2)_3SiO_{0.5}$ units and $SiO_2$ units, or
      (b) $(R^3)_3SiO_{0.5}$ units, $(R^3)_2SiO$ units and $SiO_2$ units, or mixtures thereof, where $R^2$ and $R^3$ are selected from the group consisting of vinyl radicals and monovalent hydrocarbon radicals free of aliphatic unsaturation, where from about 1.5 to about 10 mole percent of the silicon atoms contain silicon-bonded vinyl groups, where the ratio of monofunctional units to tetrafunctional units is from about 0.5:1 to about 1:1, and the ratios of difunctional units to tetrafunctional units ranges up to about 0.1:1;
   (iii) 0.02 to 2 parts of a platinum or platinum containing catalyst; and
   (iv) 50 to 100 parts of a liquid organohydrogenpolysiloxane having the formula:

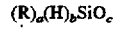

wherein c=(4−a−b)/2, b is in the range of 0.3 to 0.35, and the sum of a and b is in the range of 2.0 to 2.7.

2. The porous, non-rigid, shear thinned silicone polymer composition of claim 1 wherein said composition has a 20–50% reduction in physical entanglements relative to a similar composition that has not been shear thinned.

3. The porous non-rigid, shear thinned silicone polymer composition of claim 1 wherein said composition has a 30% reduction in physical entanglements relative to a similar composition that has not been shear thinned.

4. The porous, non-rigid, shear thinned silicone polymer composition of claim 1 wherein said composition has a 10–30% reduction in chemical reactive sites relative to a similar composition that has not been shear thinned.

5. The porous, non-rigid, shear thinned silicone polymer composition of claim 1 wherein said composition has a 20% reduction in chemical reactive sites relative to a similar composition that has not been shear thinned.

6. The porous, non-rigid, shear thinned silicone polymer composition of claim 1 wherein said composition has a predetermined moisture vapor transport rate.

* * * * *